United States Patent
Keady et al.

(10) Patent No.: US 8,550,206 B2
(45) Date of Patent: Oct. 8, 2013

(54) METHOD AND STRUCTURE FOR ACHIEVING SPECTRUM-TUNABLE AND UNIFORM ATTENUATION

(75) Inventors: John Patrick Keady, Fairfax Station, VA (US); John G. Casali, Christiansburg, VA (US); Kichol Lee, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 13/485,466

(22) Filed: May 31, 2012

(65) Prior Publication Data
US 2012/0305329 A1    Dec. 6, 2012

Related U.S. Application Data

(60) Provisional application No. 61/491,447, filed on May 31, 2011.

(51) Int. Cl.
*A61B 7/02*    (2006.01)
*E04B 1/82*    (2006.01)

(52) U.S. Cl.
USPC .......................................... 181/135; 181/284

(58) Field of Classification Search
USPC .................................................. 181/135, 284
See application file for complete search history.

(56) References Cited

U.S. PATENT DOCUMENTS

| | | | |
|---|---|---|---|
| 2,850,012 A | 9/1958 | Becker | |
| 2,876,767 A | 3/1959 | Nathan | |
| 3,110,356 A | 11/1963 | Mendelson | |
| 3,505,999 A | 4/1970 | Harvey et al. | |
| 3,602,654 A * | 8/1971 | Victoreen | 181/135 |
| 4,006,796 A | 2/1977 | Coehorst | |
| 4,029,083 A | 6/1977 | Baylor | |
| 4,060,080 A | 11/1977 | Akiyama | |
| 4,232,084 A * | 11/1980 | Tate | 428/321.5 |
| 4,834,211 A | 5/1989 | Bibby et al. | |
| 4,896,679 A | 1/1990 | St. Pierre | |

(Continued)

FOREIGN PATENT DOCUMENTS

WO    2011163565 A    12/2011

OTHER PUBLICATIONS

Allen, C. H. and E. H. Berger: Development of a unique passive hearing protector with level-dependent and flat attenuation characteristics. Noise Control Engineering Journal, 34(3), 97-105 (1990).

(Continued)

*Primary Examiner* — Forrest M Phillips
(74) *Attorney, Agent, or Firm* — New River Valley IP Law; Michele L. Mayberry

(57) ABSTRACT

The present invention relates hearing protection devices for the human ear. More particularly, embodiments of the invention provide hearing protection devices capable of tunable acoustic attenuation. The invention relates further to ear plugs comprising a fluid-containing balloon for occlusion of the ear canal, which are capable of being adjusted for example by modifying fluid composition and/or fluid pressure within the balloon to vary attenuation at different frequencies of the audible sound spectrum. Other embodiments provide an earplug with fixed attenuation comprising: a body of compressible/expandable-recovery material shaped and sized to fit in an ear canal; and at least one chamber disposed within the body and comprising a filler material chosen from at least one of water, aphrons, water with solid or gelatinous particles suspended, and oil with particles suspended.

19 Claims, 26 Drawing Sheets

(56) References Cited

U.S. PATENT DOCUMENTS

| | | | |
|---|---|---|---|
| 4,913,165 A | 4/1990 | Fishgoyt | |
| 5,131,411 A | 7/1992 | Casali et al. | |
| 5,333,622 A | 8/1994 | Casali et al. | |
| 6,368,288 B2 | 4/2002 | Stone | |
| 6,368,289 B2 | 4/2002 | Stone | |
| 6,440,102 B1 | 8/2002 | Arenberg et al. | |
| 7,171,371 B2 | 1/2007 | Goldstein | |
| 7,756,281 B2 | 7/2010 | Goldstein et al. | |
| 7,779,844 B2 * | 8/2010 | Purcell et al. | 128/865 |
| 7,817,803 B2 | 10/2010 | Goldstein | |
| 7,822,219 B2 | 10/2010 | Baker et al. | |
| 7,837,008 B1 * | 11/2010 | Lane et al. | 181/284 |
| 7,882,928 B2 * | 2/2011 | McMahon et al. | 181/135 |
| 7,886,745 B2 | 2/2011 | Purcell et al. | |
| 7,913,696 B2 * | 3/2011 | Purcell et al. | 128/864 |
| 8,018,328 B2 | 9/2011 | Goldstein et al. | |
| 8,047,207 B2 | 11/2011 | Perez et al. | |
| 8,081,780 B2 | 12/2011 | Goldstein et al. | |
| 8,111,839 B2 | 2/2012 | Goldstein et al. | |
| 8,142,870 B2 | 3/2012 | Keady | |
| 8,150,043 B2 | 4/2012 | Goldstein et al. | |
| 8,150,044 B2 | 4/2012 | Goldstein et al. | |
| 8,155,361 B2 * | 4/2012 | Schindler | 381/329 |
| 8,170,228 B2 | 5/2012 | Goldstein et al. | |
| 8,194,864 B2 | 6/2012 | Goldstein et al. | |
| 8,194,865 B2 | 6/2012 | Goldstein et al. | |
| 8,199,919 B2 | 6/2012 | Goldstein et al. | |
| 8,208,644 B2 | 6/2012 | Goldstein et al. | |
| 8,208,652 B2 | 6/2012 | Keady | |
| 8,213,629 B2 | 7/2012 | Goldstein et al. | |
| 8,213,649 B2 | 7/2012 | Goldstein et al. | |
| 8,221,860 B2 | 7/2012 | Keady | |
| 8,221,861 B2 | 7/2012 | Keady | |
| 8,229,128 B2 | 7/2012 | Keady | |
| 8,251,925 B2 | 8/2012 | Keady et al. | |
| 8,311,228 B2 | 11/2012 | Goldstein et al. | |
| 8,312,960 B2 | 11/2012 | Keady | |
| 8,315,400 B2 | 11/2012 | Goldstein et al. | |
| 8,319,620 B2 | 11/2012 | Usher et al. | |
| 8,326,628 B2 | 12/2012 | Goldstein et al. | |
| 8,326,635 B2 | 12/2012 | Usher et al. | |
| 8,437,492 B2 | 5/2013 | Goldstein et al. | |
| 8,447,031 B2 | 5/2013 | Usher et al. | |
| 2002/0143242 A1 | 10/2002 | Nemirovski | |
| 2006/0042868 A1 * | 3/2006 | Berg et al. | 181/135 |
| 2007/0270988 A1 | 11/2007 | Goldstein et al. | |
| 2008/0015463 A1 | 1/2008 | Goldstein | |
| 2008/0031475 A1 | 2/2008 | Goldstein | |
| 2008/0037797 A1 | 2/2008 | Goldstein et al. | |
| 2008/0046246 A1 | 2/2008 | Goldstein et al. | |
| 2008/0130906 A1 | 6/2008 | Goldstein et al. | |
| 2008/0137873 A1 | 6/2008 | Goldstein | |
| 2008/0144840 A1 | 6/2008 | Goldstein et al. | |
| 2008/0144841 A1 | 6/2008 | Goldstein et al. | |
| 2008/0144842 A1 | 6/2008 | Goldstein et al. | |
| 2008/0176289 A1 | 7/2008 | Zeng et al. | |
| 2008/0178088 A1 | 7/2008 | Goldstein et al. | |
| 2008/0181419 A1 | 7/2008 | Goldstein et al. | |
| 2008/0181442 A1 | 7/2008 | Goldstein et al. | |
| 2008/0205660 A1 | 8/2008 | Goldstein | |
| 2008/0212787 A1 | 9/2008 | Goldstein et al. | |
| 2008/0219456 A1 | 9/2008 | Goldstein et al. | |
| 2008/0219486 A1 | 9/2008 | Goldstein et al. | |
| 2008/0240458 A1 | 10/2008 | Goldstein et al. | |
| 2008/0253583 A1 | 10/2008 | Goldstein et al. | |
| 2008/0267416 A1 | 10/2008 | Goldstein et al. | |
| 2008/0299339 A1 | 12/2008 | Keady | |
| 2008/0311324 A1 | 12/2008 | Keady | |
| 2009/0016541 A1 | 1/2009 | Goldstein et al. | |
| 2009/0016542 A1 | 1/2009 | Goldstein et al. | |
| 2009/0022294 A1 | 1/2009 | Goldstein et al. | |
| 2009/0022353 A1 | 1/2009 | Goldstein et al. | |
| 2009/0028356 A1 | 1/2009 | Ambrose et al. | |
| 2009/0034765 A1 | 2/2009 | Boillot et al. | |
| 2009/0067661 A1 | 3/2009 | Keady et al. | |
| 2009/0071486 A1 | 3/2009 | Perez et al. | |
| 2009/0071487 A1 | 3/2009 | Keady | |
| 2009/0130423 A1 | 5/2009 | Keady | |
| 2009/0146799 A1 | 6/2009 | Goldstein et al. | |
| 2009/0147966 A1 | 6/2009 | Mcintosh et al. | |
| 2009/0154748 A1 | 6/2009 | Baker et al. | |
| 2009/0155518 A1 | 6/2009 | Keady | |
| 2009/0192407 A1 | 7/2009 | Keady et al. | |
| 2009/0214072 A1 | 8/2009 | Staab et al. | |
| 2009/0220096 A1 | 9/2009 | Usher et al. | |
| 2009/0238374 A1 | 9/2009 | Keady | |
| 2009/0238386 A1 | 9/2009 | Usher et al. | |
| 2009/0240497 A1 | 9/2009 | Usher et al. | |
| 2009/0245530 A1 | 10/2009 | Keady | |
| 2009/0264161 A1 | 10/2009 | Usher et al. | |
| 2009/0290721 A1 | 11/2009 | Goldstein et al. | |
| 2010/0002897 A1 | 1/2010 | Keady | |
| 2010/0012420 A1 | 1/2010 | Keady | |
| 2010/0033313 A1 | 2/2010 | Keady et al. | |
| 2010/0071707 A1 | 3/2010 | Wohl | |
| 2010/0074451 A1 | 3/2010 | Usher et al. | |
| 2010/0076793 A1 | 3/2010 | Goldstein et al. | |
| 2010/0135502 A1 | 6/2010 | Keady et al. | |
| 2010/0142715 A1 | 6/2010 | Goldstein et al. | |
| 2010/0142725 A1 | 6/2010 | Goldstein et al. | |
| 2010/0177918 A1 | 7/2010 | Keady et al. | |
| 2010/0241256 A1 | 9/2010 | Goldstein et al. | |
| 2010/0322454 A1 | 12/2010 | Ambrose et al. | |
| 2011/0079227 A1 | 4/2011 | Turcot et al. | |
| 2011/0085689 A1 | 4/2011 | Keady | |
| 2011/0115626 A1 | 5/2011 | Goldstein et al. | |
| 2011/0228963 A1 | 9/2011 | Goldstein et al. | |
| 2011/0235843 A1 | 9/2011 | Keady et al. | |
| 2011/0311079 A1 | 12/2011 | Keady | |
| 2012/0101514 A1 | 4/2012 | Keady et al. | |
| 2012/0103346 A1 | 5/2012 | Keady | |
| 2012/0123573 A1 | 5/2012 | Goldstein et al. | |
| 2012/0177209 A1 | 7/2012 | Goldstein et al. | |
| 2012/0177210 A1 | 7/2012 | Goldstein et al. | |
| 2012/0288104 A1 | 11/2012 | Goldstein et al. | |
| 2013/0035608 A1 | 2/2013 | Goldstein et al. | |
| 2013/0039518 A1 | 2/2013 | Goldstein et al. | |
| 2013/0098706 A1 | 4/2013 | Keady | |
| 2013/0123919 A1 | 5/2013 | Goldstein Steven et al. | |

OTHER PUBLICATIONS

Casali, J. G. and Berger, E H. Technology advancements in hearing protection: Active noise reduction, frequency/amplitude-sensitivity, and uniform attenuation. American Industrial Hygiene Association Journal, 57,175-185. (1996).

Casali, J. G. and Gerges, S., Protection and enhancement of hearing in noise, in Williges, R. C., Ed. Reviews of Human Factors and Ergonomics, vol. 2. Human Factors and Ergonomics Society Santa Monica, CA, 7,195-240, (2006).

Casali, J. G., Advancements in hearing protection: Technology, applications, and challenges for performance testing and product labeling. Proceedings of the 2005 International Congress and Exhibition of Noise-Control Engineering, Rio de Janeiro, Brazil, 2097-2118 (2005).

Casali, J. G., Ahroon, W. A., and Lancaster, J. A field investigation of hearing protection and hearing enhancement in one device: For soldiers whose ears and lives depend upon it. Noise and Health Journal, 11(42), 69-90 (2009).

Casali, J. G., Mauney, D. W., and Burks, J. A. Physical vs. psychophysical measurement of hearing protector attenuation—a.k.a. MIRE vs. REAT. Sound and Vibration, 29(7), 20-27, (1995).

Casali, J. G., Passive Augmentations in Hearing Protection Technology Circa 2010: Flat-Attenuation, Passive Level-Dependent, Passive Wave Resonance, Passive Adjustable Attenuation, and Adjustable-Fit Devices: Review of Design, Testing, and Research. International Journal of Acoustics and Vibrations, 15(4), 187-195 (Dec. 2010).

Casali, J. G., Powered Electronic Augmentations in Hearing Protection Technology Circa 2010 including Active Noise Reduction, Electronically-Modulated Sound Transmission, and Tactical Communications Devices: Review of Design, Testing, and Research. International Journal of Acoustics and Vibrations, 15(4), 168-186 (Dec. 2010).

(56) References Cited

OTHER PUBLICATIONS

Gerges, S. and Casali, J. G., Hearing protectors, in Crocker, M., Ed. Handbook of Noise and Vibration Control, John Wiley, New York, 31, 359-372, (2007).

Lee, Kichol, "Effects of Earplug Material, Insertion Depth, and Measurement Technique on Hearing Occlusion Effect", Dissertation submitted to the Faculty of the Virginia Polytechnic Institute and State University, Jan. 21, 2011, Blacksburg, Virginia.

Mosko, J. D. and Fletcher, J. L., Evaluation of the Gunfender earplug: Temporary threshold shift and speech intelligibility. Journal of the Acoustical Society of America, 49, 1732-1733 (1971).

Perala, C. H. and Casali, J. G. Human subject investigation of MIRE microphone location during insertion loss testing of Active Noise Reduction hearing protectors in active and passive modes. Noise Control Engineering Journal, 57(5), 442-458, Sep.-Oct. 2009.

Suter, A. H., The effects of hearing protectors on speech communication and the perception of warning signals (AMCMS Code 611102.74A0011), Aberdeen Proving Ground, MD: U.S. Army Human Engineering Laboratory, 1-32, (1989).

Witt, B. Can you hear flat?? Proceedings (on CD) of the 31st Annual National Hearing Conservation Association Conference, Tampa, FL, Feb. 16-18, 2006.

International Preliminary Report on Patentability for International Application No. PCT/US2011/041776 dated Dec. 28, 2012.

International Search Report of International Application No. PCT/US2011/041776 dated Oct. 28, 2011.

\* cited by examiner

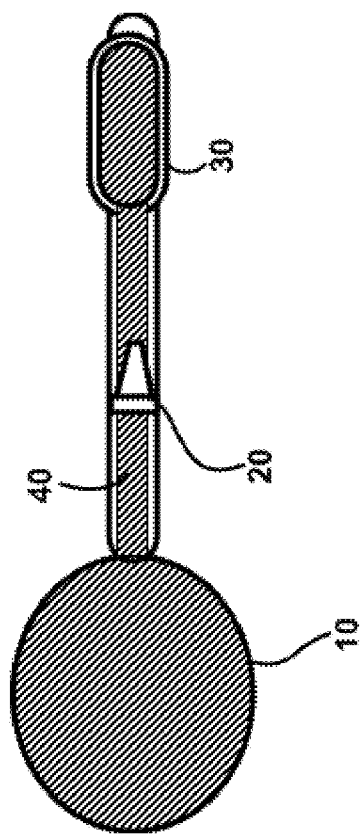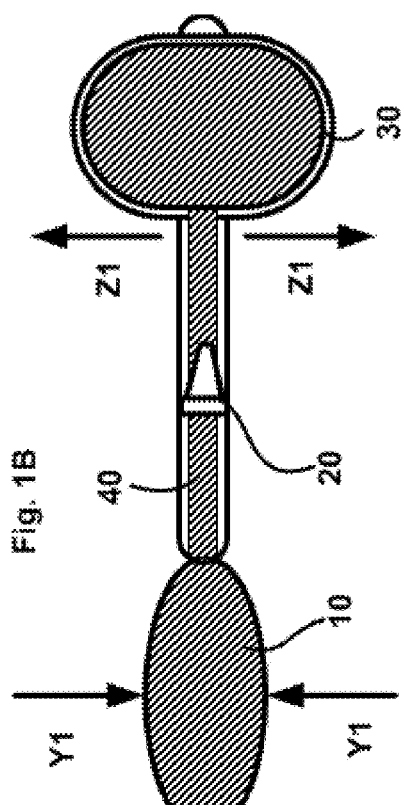

ER-20 Hi-Fi™ Earplug (pre-molded)

Model ER-15 Custom - Molded Flat - Attenuation Earplug

ER-15 Musician's Earplug (custom molded)

Combat Arms™ single-ended earplug with rocker valve to change attenuation state.

Combat Arms™ double-ended earplug.

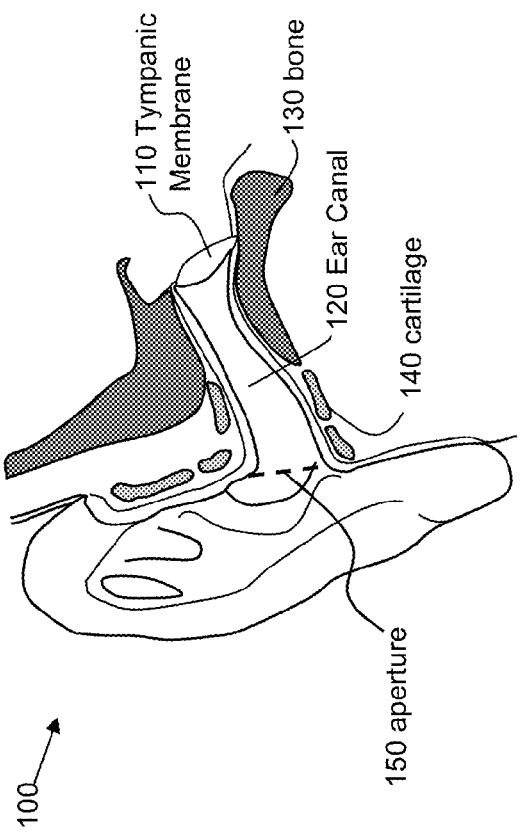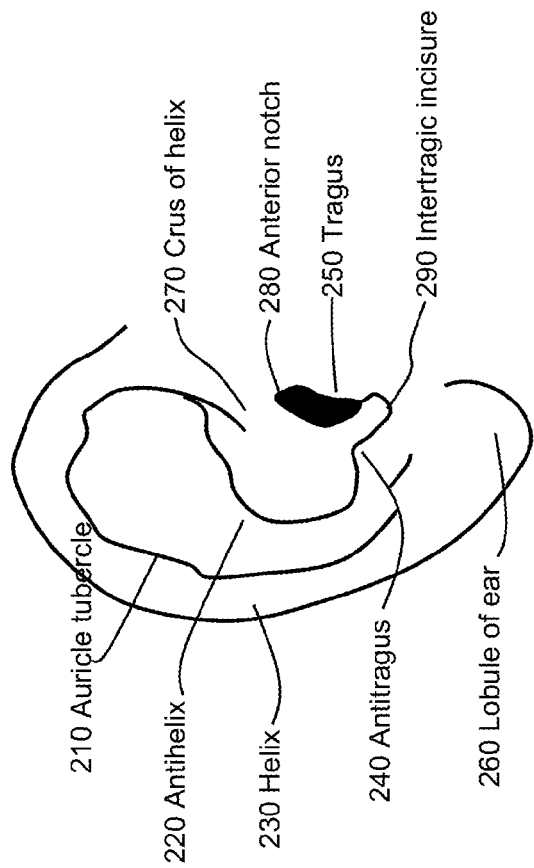
FIG. 5
FIG. 6

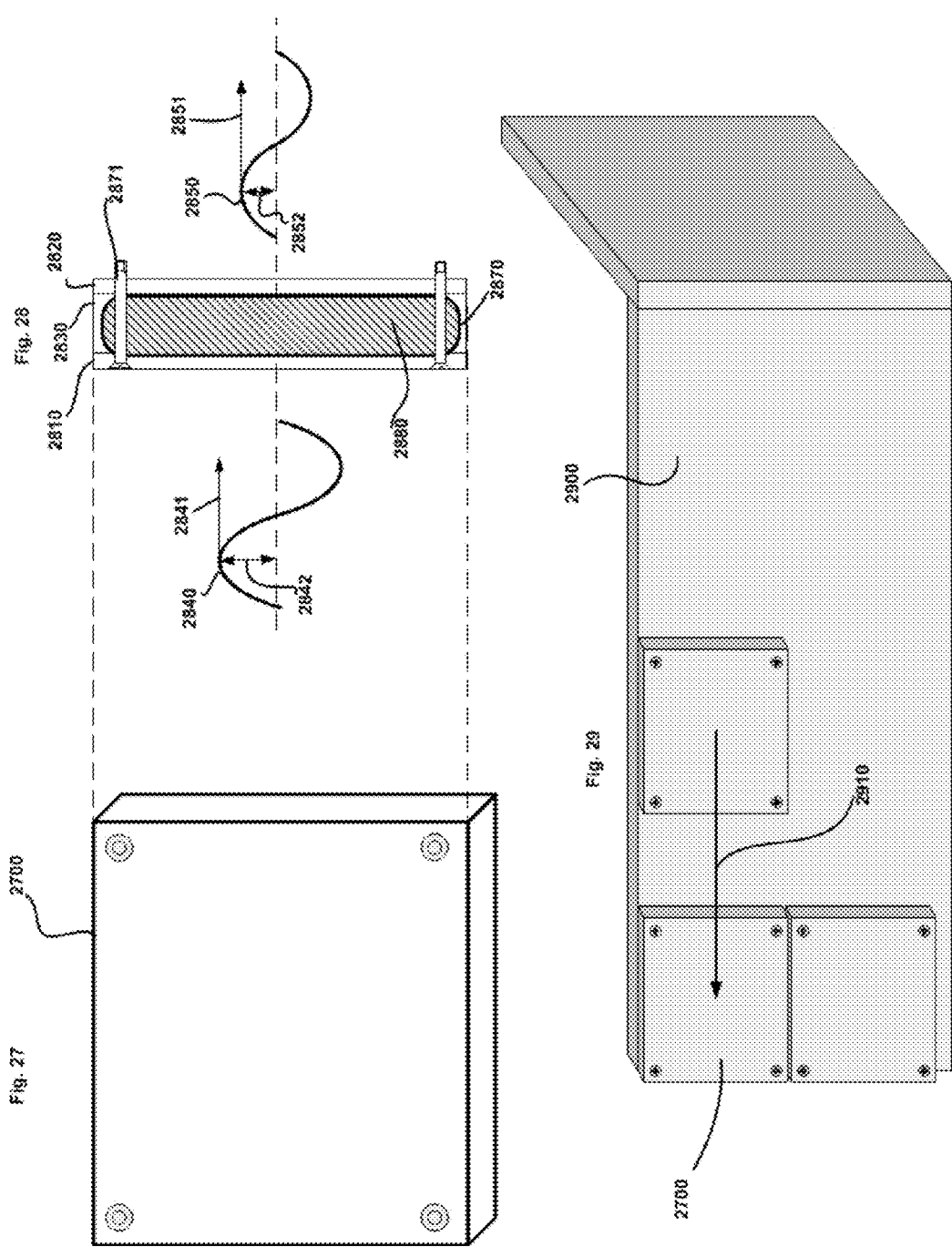

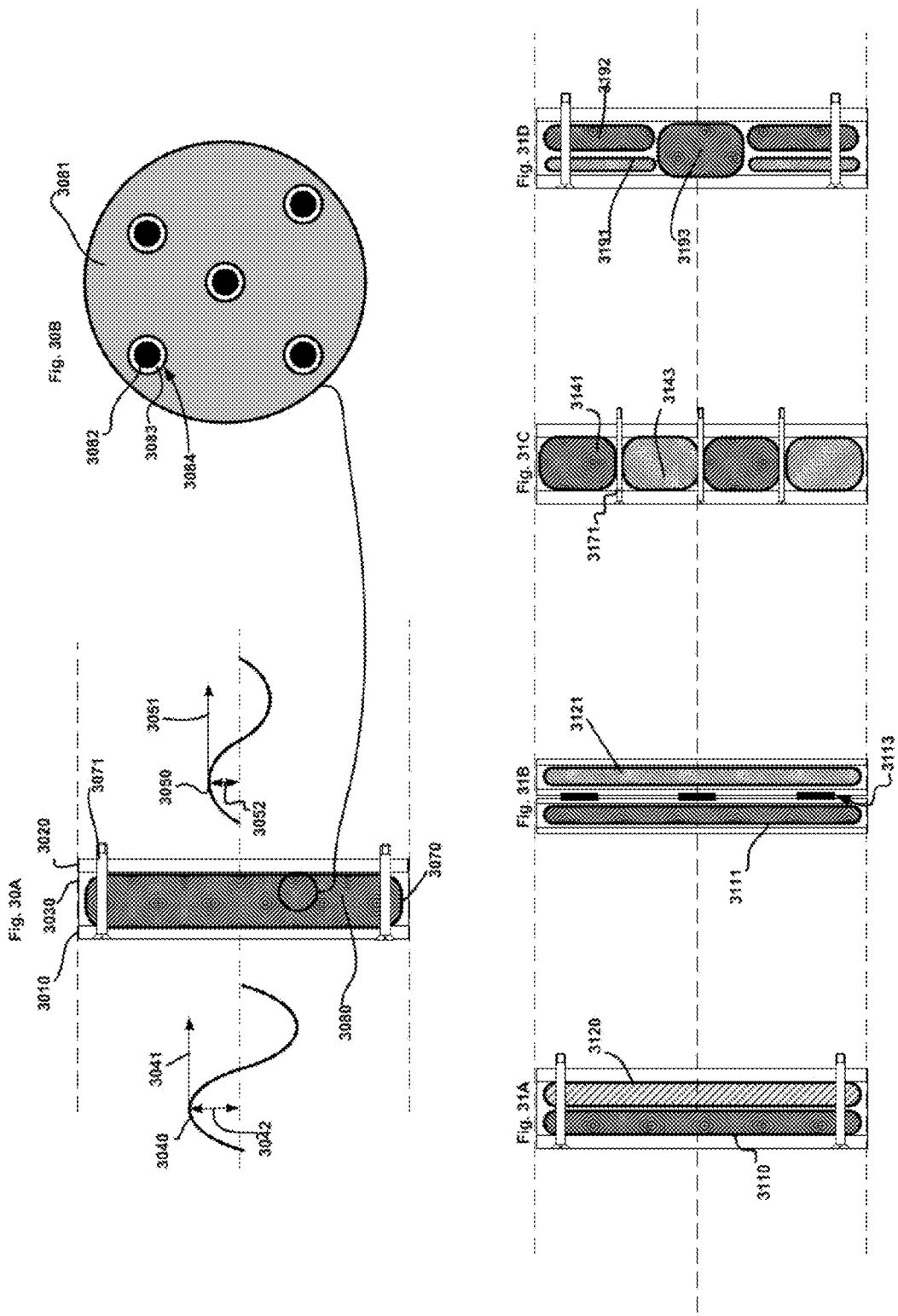

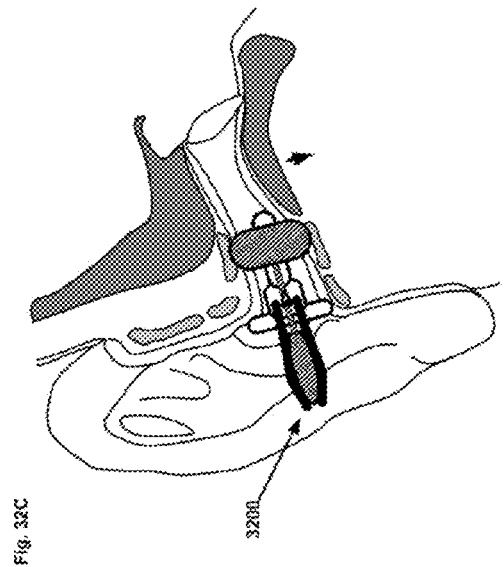
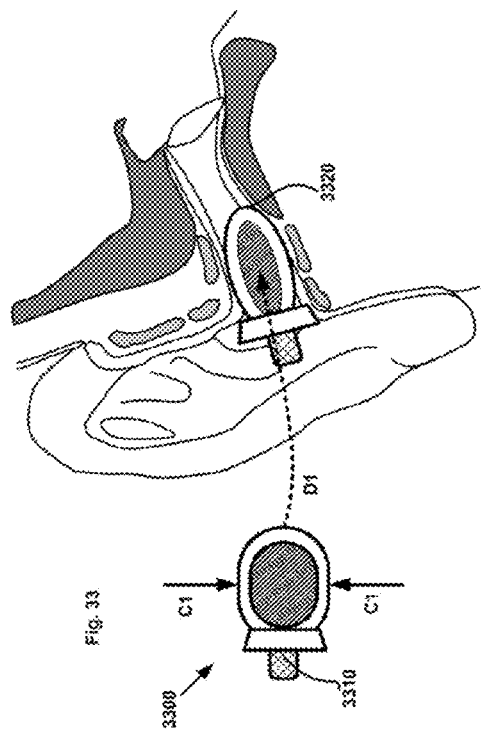
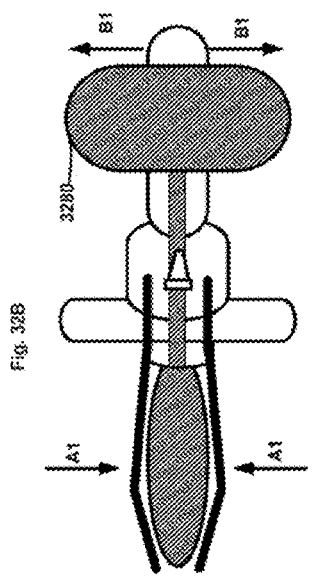
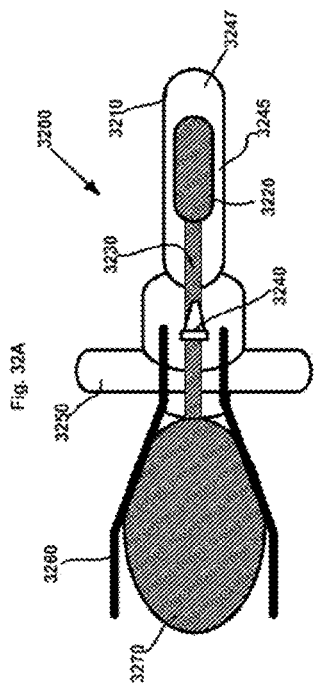

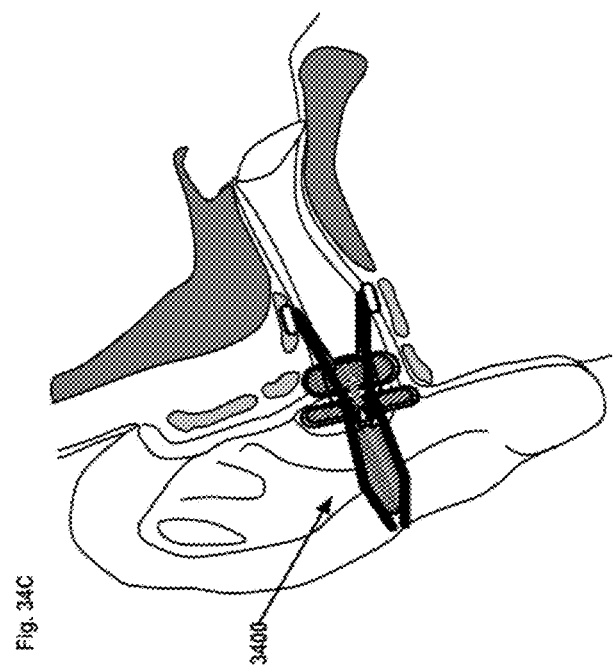
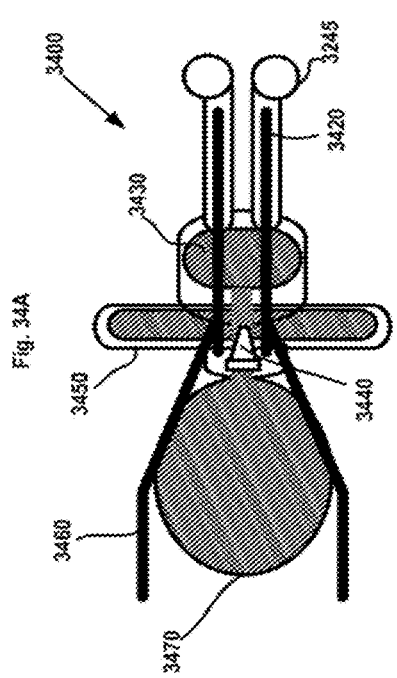
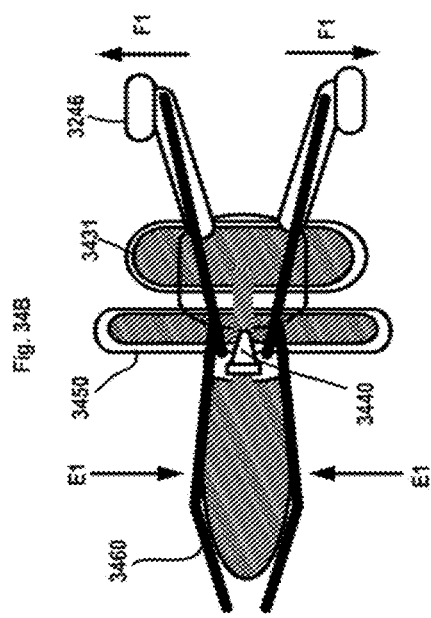

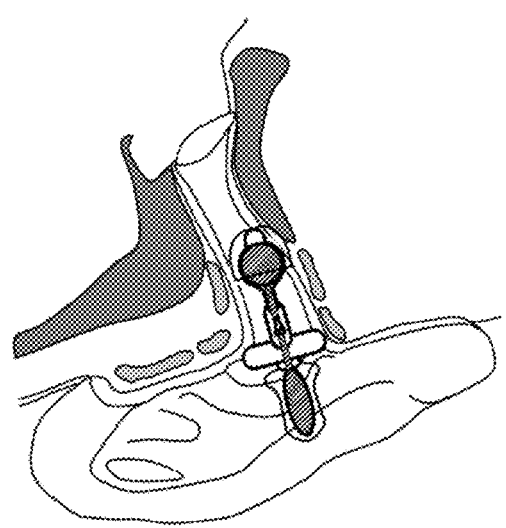
Fig. 36
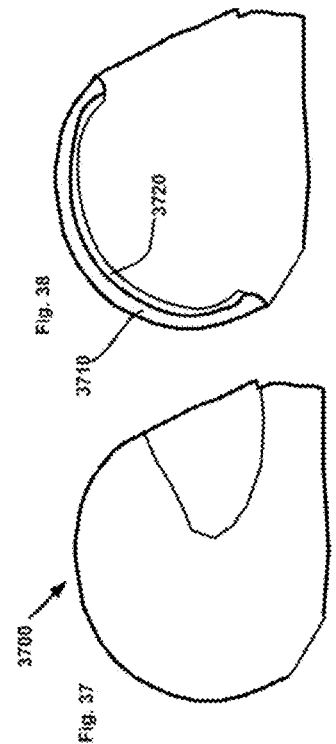
Fig. 38
Fig. 37
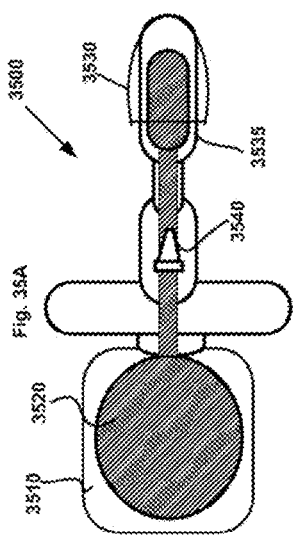
Fig. 35A
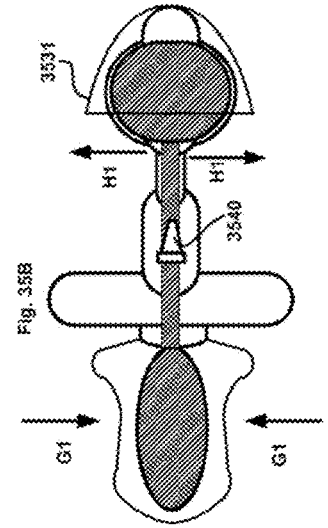
Fig. 35B
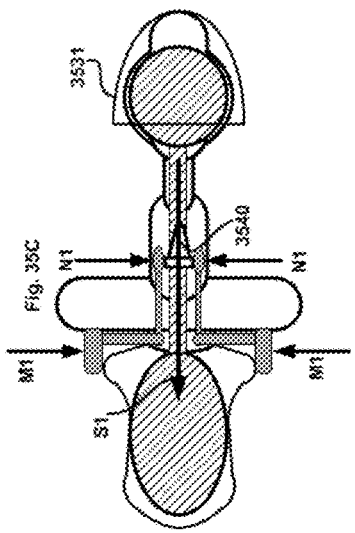
Fig. 35C

METHOD AND STRUCTURE FOR ACHIEVING SPECTRUM-TUNABLE AND UNIFORM ATTENUATION

CROSS-REFERENCE TO RELATED APPLICATIONS

This application claims priority to and the benefit of the filing date of U.S. Provisional Patent Application No. 61/491,447, filed May 31, 2011, the disclosure of which is incorporated herein by reference in its entirety.

BACKGROUND OF THE INVENTION

1. Field of the Invention

The present invention relates to acoustic shaping devices. More particularly, embodiments of the invention provide devices and methods for shaping the acoustic spectrum passing through a device.

2. Description of Related Art

As one example of an acoustic shaping device, conventional hearing protection devices (HPDs) are generally delineated into passive (non-electronic) and active (powered electronic) designs. See Casali, J. G., Advancements in hearing protection: Technology, applications, and challenges for performance testing and product labeling. Proceedings of the 2005 International Congress and Exhibition of Noise-Control Engineering, Rio de Janeiro, Brazil, 2097-2118 (2005) ("Casali 2005"). Passive HPDs are further categorized as earplugs, ear canal caps, earmuffs, and helmets, based on the location of the sealing and design configuration. See Gerges, S. and Casali, J. G., Ear protectors, in Crocker, M., Ed. Handbook of Noise and Vibration Control, John Wiley, New York, 31, 364-376, (2007) ("Gerges and Casali, 2007").

Passive HPDs generally attenuate noise through static, passive means. Most hearing protection fails to deliver a flat attenuation (that is, equivalent or near-equivalent reduction of sound) across the frequency spectrum. Instead, attenuation typically increases in decibels (dB) as the frequency increases in a non-linear manner. This non-linear behavior affects the perception of sound frequencies across the audible spectrum in different degrees and creates an unnatural imbalance in perceiving sound pitch. As a result, pitch perception and other auditory experiences which rely on frequency-based cues can be compromised by the non-linear attenuation imparted by conventional hearing protectors.

For example, earmuffs, on average more so than earplugs, tend to attenuate high-frequency sound more than low frequency sound, thereby reducing the power of consonant sounds that are important for word discrimination and which lie in the higher frequency range (Gerges and Casali, 2007). The sloping, nonlinear attenuation profile versus frequency, which provides higher attenuation values with increasing frequency, creates a spectral imbalance from the listener's perspective. This imbalance occurs because the relative amplitudes of different frequencies are heard differently than they would be without the conventional HPD, that is, with the open ear, and thus broadband acoustic signals are heard as spectrally different from normal. In other words, the sounds are often reported as more bassy and resonant. Thus, the spectral quality of a sound is altered, and sound interpretation, which is important in certain aural tasks, may suffer as a result. Thus, there is a desire for uniform (or flat) attenuation HPDs, since these devices tend not to bias the hearing of sounds across the audible frequency range.

Although on average, earmuffs display a larger imbalance between their low and high-frequency attenuation than do earplugs, some earplugs demonstrate substantial spectral nonlinearities in their attenuation. This is shown in the two lowermost functions of FIG. 2. When listening to a sound while wearing such conventional earplugs (or an earmuff), all pitches that compose the sound are reduced in level, but due to the influence of the nonlinear attenuation, the amplitudes of various pitches are also changed relative to one another in a non-uniform manner across the spectrum, rendering the wearer's hearing of the sound as distorted when compared to its perception with the unoccluded ear. Accordingly, in many situations there is a need for uniform or "flat" attenuation, such as pitch perception by musicians, cutting speed/friction by machinists, impending bearing failures by helicopter pilots, and "roof talk" by underground miners to name a few.

In an attempt to counter these effects, in the early 1990s, flat or uniform attenuation HPDs were developed by AEARO-3M and Etymotic Research, Inc., including the Etymotic ER-15 Musician's custom-molded earplug and the ER-20 HiFi™ pre-molded earplug. See Casali, J. G. and Berger, E. H. Technology advancements in hearing protection: Active noise reduction, frequency/amplitude-sensitivity, and uniform attenuation. American Industrial Hygiene Association Journal, 57, 175-185. (1996) ("Casali 1996"). As illustrated in FIGS. 3A-B, these devices use acoustical damping and filtering networks, as well as unique placement of the sound entry port near the ear canal's rim, to provide essentially flat attenuation over the range of frequencies from 125 Hz to 8000 Hz. Attenuation of these devices is shown in FIG. 2 (uppermost functions).

Another, different, class of HPDs are passive, level-dependent HPDs which are designed so that their attenuation increases as the ambient noise level increases. Such devices rely upon acoustical networks, mechanical ball or flutter valves, or orifices in blocked sound ports which respond dynamically to intense air pressure changes to activate their unique attenuation responses. One of the earliest designs in this category was a dynamically-valved earplug named the Gunfender™, and the North Safety Co. followed with a device called the Sonic Ear-Valve™. See Mosko, J. D. and Fletcher, J. L., Evaluation of the Gunfender earplug: Temporary threshold shift and speech intelligibility. Journal of the Acoustical Society of America, 49, 1732-1733. (1971). In the early 1990s, an additional earmuff style device that relied on a sharp-edged, orifice-based, controlled leakage path in a duct was E_A_R Corporation's Ultra 9000™. See Allen, C. H. and E. H. Berger: Development of a unique passive hearing protector with level-dependent and flat attenuation characteristics. Noise Control Engineering Journal, 34(3), 97-105. (1990) ("Allen 1990"). Later, using similar technology comprising a calibrated leaky filter in an acoustical duct running through the stem of an earplug, the AEARO Combat Arms™ earplug was developed for military use, which was followed by a recent commercial version named the Arc™ earplug. See Babeu, L. A., Binseel, M. S. Mermagen, T. J. and Letowski, T. R. Sound localization with the Combat Arms™ earplug. Proceedings (on CD) of the 29th Annual National Hearing Conservation Association Conference, Seattle, Wash., Feb. 19-21. (2004) ("Babeu 2004"); and Casali, J. G., Ahroon, W. A., and Lancaster, J. A field investigation of hearing protection and hearing enhancement in one device: For soldiers whose ears and lives depend upon it. Noise and Health Journal, 11(42), 69-90. (2009) ("Casali 2009"). A custom-molded earplug was introduced by Variphone Benelux N.V., the Variphone Stopgun™, which uses a nonlinear filter to attenuate impulsive noises of above about 110 dB according to the manufacturer's website: http://www.variphone.com/en/hearing-protection/shooting-sport/stopgun.

Typically, passive level-dependent HPDs provide very low attenuation in low to moderate noise levels; however, as ambient noise levels increase to a certain level, their attenuation increases to a maximum and plateaus afterwards. (Casali 1996; Allen 1990). With contemporary orifice/acoustical filter-based, level dependent HPDs at low noise levels, their passive attenuation behaves as that of a leaky protector, offering minimal attenuation below about 1000 Hz because laminar flow is present in the duct and sound passes with low impedance through the orifice. This minimal attenuation is all that is available to protect the wearer's hearing at sound levels below about 110 dB. Since such devices are intended to be used primarily in intermittent impulsive noise, this should not be a problem as long as the off periods are relatively quiet (e.g., below an A-weighted noise level of approximately 85 dB). At elevated sound pressure levels (above about 110 dB to 120 dB, as might occur during a gunshot), the flow through the orifice changes from laminar to turbulent, effectively closing the orifice and thus sharply increasing the attenuation of the device. (Allen 1990).

Due to the fact that level-dependent earplugs of the Combat Arms™ and Arc™ types provide very little protection at sound levels below an A-weighted noise level of about 110 dB, they are clearly not suitable for continuous noise exposures and are intended for intermittent exposures which entail quiet periods interrupted by sudden explosions, gunshots, arc blasts, high pressure pneumatic discharges, or similar impulsive sounds. However, to provide protection in situations wherein both intermittent quiet/impulsive noise as well as periods of continuous noise can manifest, both the Combat Arms™ and Arc™ earplugs were designed with two "ends" that afford selectable protective states, in which one end is level-dependent, and the other is a conventional passive earplug that is suitable for continuous noise exposures. (Babeu 2004; Casali 2009). An example of the first generation Combat Arms™ earplug with the level-dependent and conventional passive ends is shown in FIG. 4A. Now in its third generation, and as shown in FIG. 4B, a more recent version of the Combat Arms™ earplug incorporates a single end that is manually converted between the two aforementioned conventional and level-dependent states by a manually-operated, rocker-activated valve. An additional advantage, most relevant to attempts at producing spectral shaping as a function of frequency by mechanical means, is that some orifice-based, level-dependent HPDs, such as the AEARO-3M Ultra 9000 Earmuff™, offer roughly flat attenuation, though not the case with the level-dependent end of the Combat Arms™ earplug. See Allen 1990.

One consequence of improper attenuation in an HPD is that a user may reject the hearing protection if it compromises his/her hearing to the extent that sounds no longer appear natural, signals cannot be detected or localized, and/or speech cannot be understood. In some cases, too much attenuation may be provided by an HPD for a particular noise situation, with the concomitant effect that the user's hearing is unnecessarily degraded. In lay terms, this is commonly referred to as "overprotection." The safety professional often faces a dilemma in selecting HPDs for the workforce. They must provide adequate attenuation for the noise threat at hand, but they may not provide so much attenuation that the worker cannot hear important signals and/or speech communications—the dilemma of underprotection versus overprotection.

A major stimulus for the development of augmented HPDs has been the sometimes negative influence that conventional HPDs have on the hearing ability of users. See Casali, J. G. and Gerges, S., Protection and enhancement of hearing in noise, in Williges, R. C., Ed. Reviews of Human Factors and Ergonomics, Vol. 2. Human Factors and Ergonomics Society Santa Monica, Calif., 7, 195-240, (2006) ("Casali 2006"); and Suter, A. H., The effects of hearing protectors on speech communication and the perception of warning signals (AM-CMS Code 611102.74A0011), Aberdeen Proving Ground, Md.: U.S. Army Human Engineering Laboratory, 1-32. (1989) ("Suter 1989").

To help overcome the problem of overprotection in moderate noise environments, earplug augmentations have been developed to allow the user some level of control over the amount of attenuation achieved. These devices incorporate a leakage path that is adjustable by setting a valve that obstructs a tunnel or "vent" cut through the body of the plug, or by selecting from a choice of available filters or dampers that are inserted into the vent.

The Variphone™ is one such example of an adjustable-valve design and is constructed from an acrylic custom-molded impression of the user's ear canal. The attenuation adjustment range of the device is approximately 20 dB to 25 dB below 500 Hz, with a maximum attenuation of about 30 dB at 500 Hz. At higher frequencies, the range of adjustment decreases, while the maximum attenuation attainable increases slightly.

The Sonomax SonoCustom™ is an example of a selectable-damper design. This device can be fitted with a variety of attenuation dampers that provide the opportunity for discretely variable attenuation in a single device, and each damper has distinct spectral attenuation values and NRR. Furthermore, the SonoCustom™ HPD is sold as a system with a probe tube microphone test apparatus which verifies the amount of attenuation achieved by way of MIRE techniques on each user as they are fit with the product.

There is also a full custom-molded option of the acrylic Variphone™ brand earplug as well as the silicone V-SIL™, both of which incorporate a duct into which selectable "filters" are inserted for different attenuation values. Another device is the dB Blocker™ from Custom Protect Ear. This product is a vented, custom-molded earplug that offers different cartridge filters that can be inserted into the vent. Each cartridge comprises a unique damper/filter which affords a specific attenuation spectrum, and the selection of cartridge is based upon an analysis of the wearer's noise exposure and other needs. The cartridge is intentionally not user-replaceable, so the dB Blocker™ is returned to the manufacturer should a cartridge need replacement or changing.

Two important distinctions between passive adjustable-attenuation HPDs and passive level-dependent HPDs is that the former require user or manufacturer setting to effect attenuation changes, and the attenuation, once selected, is essentially independent of incident sound level, that is, level-independent. On the other hand, level-dependent devices react automatically to changes in incident sound pressure levels and the user has no control over the change in attenuation when the HPD is worn in its level-dependent configuration.

Attenuation testing of adjustable attenuation passive devices is only slightly more complex than for flat-attenuation passive devices. For devices with discrete settings (e.g., the SonoCustom™ and the dB Blocker™), the EPA proposed rule specifies using the standard REAT test of ANSI S12.6-2008 for each level of adjustment (or for each damper/filter insert) and an NRR value is determined for each setting. Although this is time consuming and labor intensive, it is necessary protocol to quantify the performance at each setting or for each cartridge insert. Continuously variable devices (e.g., Variphone™) are more problematic to attenuation testing because they can only be tested reliably at the extremes of their adjustment range (i.e., fully open and fully closed). It is more difficult to reliably quantify the protection afforded by such devices at all intermediate settings, unless those intermediate settings are reproducible through a detent or graduation setting on the valve control.

The adjustable-attenuation class of HPDs affords flexibility in product development in that these devices can be designed to allow for modular augmentations, and this is potentially a major advantage in that these relatively expensive and personalized (i.e., custom- or semi-custom-molded) earplugs can then be adapted to changing user needs and different noise environments without making a new custom-molded earplug. Filter-based devices can be tuned for specific environments or tuned to pass speech or other critical bands necessary for specific jobs, assuming that the filter's passband response is properly optimized to the objective.

Due to the simple fact that a uniform HPD's relatively flat attenuation spectrum enables the listener's ears to retain their normal, albeit uniformly attenuated, frequency response, perceptual advantages of these specialized hearing protectors are obvious, and for certain user populations, such as musicians, the more natural hearing provided should prove to be beneficial. However, the purported benefits to hearing perception of flat attenuation HPDs have been tested in few studies. One notable exception was a demonstration experiment by Witt, who, in an effort to determine whether the presence of flat attenuation was noticeable by HPD users in industrial applications, recorded speech and industrial noise under varying attenuation slopes of earplugs and played them back to obtain subjects' responses. The benefits of near-flat attenuation (as achieved with a prototype of the Sperian AirSoft™ earplug) were most noticeable in industrial settings when the increase in earplug attenuation was less than a slope of 10 dB over the frequency range of 250 Hz to 4000 Hz. Furthermore, Witt noted that while the first flat attenuation devices developed in the 1990s (i.e., the ER earplugs discussed above) utilized controlled, tuned leakage paths and dynamic mechanical networks to yield their linear attenuation, advances in earplug materials in the first half of the 2000s decade have enabled near-linear attenuation in certain disposable earplugs, thus bringing the cost of uniform (or at least "near-uniform") attenuation technology down into the realm of more industrial users. Witt, B. Can you hear flat?? Proceedings (on CD) of the 31st Annual National Hearing Conservation Association Conference, Tampa, Fla., Feb. 16-18. (2006).

To achieve near-uniform attenuation with disposable devices, however, the quality of fit is important, since an acoustical leak will invariably degrade (that is, increase) the low-frequency attenuation. It is also important to recognize that "true" flat attenuation HPDs (e.g., ER-15, ER-20) that incorporate the leakage paths and mechanical networks noted above provide generally lower attenuation than that afforded by most well-designed conventional earplugs, so they are not typically appropriate for ear defense in high exposure levels. (Casali 1996; Casali 2006).

Many user-molded, conventional passive earplugs have been successful in the hearing protection marketplace. Such products are typically designed to provide a "one-size-fits-most" earplug that is constructed from a malleable or compressible/expandable-recovery material and that is larger in cross-sectional diameter than the ear canal. Typically, these user-molded products are manufactured with materials such as slow-recovery polyurethane or polyvinyl foams, finely spun fiberglass (also known as Swedish Wool™), various paraffin and beeswax-based products, or malleable putty encapsulated inside a soft plastic sheath, which are formable and/or exhibit compressible/expandable-recovery. Since their original dimension is bigger than the ear canal into which they are inserted, the recovery process creates an acoustic seal. In order to achieve a quality fit, the user must first manually "mold" or form (by way of finger-exerted compression and/or elongation force) the earplug into an "under-size" shape before it is actually inserted, and then to quickly insert it before it returns to its original shape and size. For some users, this manipulation of the earplug prior to insertion and subsequent prompt insertion can be difficult. Furthermore, foam, putty, or wax-based earplugs cannot be "dynamically" adjusted inside the canal once they have been inserted. Instead, they must be fully removed from the ear canal, and then a new molding/insertion process must commence.

Foam earplugs, such as SparkPlug® by Moldex and E-A-R Classic PVC foam earplugs, are examples of slow-recovery devices. Premolded flanged earplugs such as Ultrafit® by AEARO-3M and HOWARD LEIGHT Fusion® only require users to push them into ear canal without any premolding. Earplugs made of paraffin or beeswax will require initial premolding by the user and then a forced insertion to deform them to fit the ear canal of the user.

Custom-molded earplugs can be made as either passive or active devices. See Casali, J. G., Passive Augmentations in Hearing Protection Technology Circa 2010: Flat-Attenuation, Passive Level-Dependent, Passive Wave Resonance, Passive Adjustable Attenuation, and Adjustable-Fit Devices: Review of Design, Testing, and Research. International Journal of Acoustics and Vibrations, 15(4), 187-195 (December 2010) ("Casali 12010"); Casali, J. G., Powered Electronic Augmentations in Hearing Protection Technology Circa 2010 including Active Noise Reduction, Electronically-Modulated Sound Transmission, and Tactical Communications Devices: Review of Design, Testing, and Research. International Journal of Acoustics and Vibrations, 15(4), 168-186 (December 2010) ("Casali II 2010").

After a custom-molded earplug is produced for a person's ear canal, it can be used by itself as a passive device that provides relatively good attenuation if the impression is usually made with a deeply-inserted ear dam. Many companies, however, such as Sonomax and Custom Protect Ear, create a pass-through channel or vent that can be fitted with various dampers that can provide different levels of attenuation. The channel or vent can also be fitted with blocks that contain electronic circuitry that can provide electronic augmentations such as noise cancellation, electronic filtering, closed-loop attenuation control, hearing assistive circuits, automatic gain control, digital signal recognition/processing, and so forth. See Casali II 2010.

Thus, a one-size-fits-all type of device capable of producing a flat (that is, relatively uniform) attenuation across the acoustic frequency spectrum, as well as a device that can be easily modified through adjustments in certain design parameters to produce attenuation that is spectrally-shaped across the frequency spectrum for shapes other than flat, and/or a device which may afford user in-situ adjustability as to spectral attenuation, would be highly desirable.

SUMMARY OF THE INVENTION

At least one exemplary embodiment for use as an earplug is illustrated in FIGS. 1A and 1B. In general the embodiment includes a deformable fluid reservoir 10, an expandable element 30, a fluid transfer channel 40, and a valve 20. The distal end (right side of FIG. 1A) is placed into the ear canal to the desired depth, then the reservoir is depressed forcing fluid through the fluid transfer channel 40 into the expandable element 30. The valve prevents flow back from the expandable element 30 into the reservoir 10. Pressure and composition of the fluid can be modified to provide a targeted modification of the acoustic spectrum (acoustic shaping) passing through the earplug. Note that at least one exemplary embodiment does not include a valve, and yet another can include multiple valves, for example a return valve can be included in FIG. 1A such that upon pulling if the pressure on the expandable element 30 reaches a particular value (e.g., 200 mbar gauge pressure) then the flow will proceed from the expandable element 30 back to the reservoir 10.

Once inserted into place, and resting at a comfortable depth that can be limited by an optional "stop flange" or "safety limiter flange" on the outside of the balloon, the user manually inflates the balloon to fit his/her ear canal at a comfortable pressure using a few presses of the integrated manual pump that is located outside of the ear canal but in the concha region. According to embodiments of the invention, the safety limiter flange need not be of any particular shape or size, so long as it provides means for preventing the device inserted in an ear from being inserted too far into the ear canal. Some designs are provided in the figures that accompany this specification, however, any number of alternative configurations can also be used so long as the mechanism performs this intended function. Such adjustable-size inserts can comprise a stent or tube though the center of the balloon to provide a sound pathway duct, and at its distal end, a tiny fingertip pump to inflate the balloon once it is in the ear canal (FIG. 1). In this example, the adjustment of the balloon pressure is considered dynamic because the user can, at any time, deflate or readjust pressure after the balloon is inserted into the ear. The pump is optionally integrated with a module that can house electronics, batteries, microphones, or other features. The pass-through sound port can be eliminated or plugged to achieve a purely passive HPD, or it can remain open for venting or transmission of signals or speech from a tiny loudspeaker in the device's outer module.

New developments have been made to overcome the common "oversize" disadvantage presented by user-molded earplugs (see, for example, Casali I, 2010). At least one exemplary embodiment of the invention uses an expandable distal end of an earplug (e.g., expandable tube, balloon for example angioplasty balloon technology). Ear inserts using this technology are capable of being dynamically adjustable. The expandable distal end earplug design is different from conventional earplugs in that its initial dimension is smaller than that of the ear canal. Users can insert them without initial compression or pre-molding. After insertion, the distal end is then expanded (e.g., if the distal end is a balloon on a stent then the balloon can be expanded) to create an acoustic seal. Such expandable distal end hearing protection devices attenuate acoustic energy before it reaches the eardrum (tympanum) by creating an insertion loss that is achieved by reflection of the sound waves, dissipation within the expandable distal end and entrapped medium therein, acoustical impedance, and stiffening of the ear canal walls through contact thereto. According to this specification the term distal end refers to the end of the ear device that is inserted into the ear and is opposite the proximal end which comprises the control mechanism for the device.

An example of balloon technology is discussed in U.S. Published Patent Application Nos. 20090022353 to Goldstein and Keady and 20090245530 to Keady, which are incorporated by reference herein in their entireties, are distinguished from conventional HPDs in that the balloon and support structure are well under the size of the cross-sectional area of the ear canal and thus can be inserted without user manipulation. Note that the expandable distal end need not be a balloon, for example it can be an expandable end tube (with thinner tube walls in the region of expansion), a foam with a chamber in which a medium can be inserted or withdrawn, electrically expandable and contracting mediums. At least one exemplary embodiment of the invention provides an array of HPDs that allow for one or more of: user-adjustable attenuation; methods of adjusting attenuation across a range of frequencies; and/or flat or uniform attenuation across a range of frequencies.

A preferred embodiment of the invention includes an earplug system comprising: a user controllable pump inoperable communication with a fluid inlet of a lengthwise passageway terminating at a fluid outlet in operable communication with a balloon, wherein during use the balloon is inflatable with fluid by activating the pump to increase or decrease the amount of fluid in the balloon. Adjusting the fluid pressure in the balloon is performed by the user of the device to adjust attenuation. Attenuation can also be adjusted by altering the composition of the fluid in the balloon.

Earplug systems can further comprise a sound pathway duct disposed lengthwise through the stent, substantially parallel to the fluid passageway.

Specific embodiments of the invention can include an earplug comprising: a balloon or other expandable or inflatable container; a pump insert port operably configured to attach to a detachable pump system in a manner to pump fluid into the balloon from the pump when activated; and a pump seal valve operably configured to close when the pump system is detached from the pump insert port. Further embodiments include a pump which comprises means for altering fluid composition.

Also included within the scope of the invention is an earplug system comprising: a first fluid reservoir; a second fluid reservoir; a lanyard (e.g., hollow tube or passageway) operatively connecting the first fluid reservoir and the second fluid reservoir; and a pump in operable communication with the lanyard, wherein the pump is capable of modifying fluid pressure in the first and second fluid reservoirs.

Embodiments of the invention additionally include an earplug comprising: a stent with a fluid passageway disposed lengthwise therethrough and having a fluid inlet and a fluid outlet; a balloon disposed at a distal lengthwise end of the stent and in operable communication with the fluid outlet in a manner to receive fluid from the stent; a second balloon disposed at a proximal lengthwise end of the stent and in operable communication with the fluid inlet; a housing disposed at the proximal end of the stent and encompassing the fluid inlet and the second balloon, wherein the housing comprises a hollow cylindrical interior portion with a threaded interior surface; and a plunger for depressing the second balloon in a manner to push fluid from the second balloon into the first balloon, wherein the plunger comprises a disk shaped head threaded around its circumference in a manner to engage with the threaded interior surface of the housing; wherein during use the plunger is capable of being rotated within the housing to depress the second balloon and produce a pressure to inflate the first balloon, or is capable of being counter rotated to release depression of the second balloon and deflate the first balloon.

Such ear devices can be configured such that the fluid contained within the system or device is air and the pressure is about 400 mbar to obtain a flatter attenuation profile between acoustic frequencies of about 125 Hz and about 8 kHz than with a lower pressure.

Preferred embodiments may include an earplug comprising: a body of compressible/expandable-recovery material shaped and sized to fit in an ear canal; and at least one chamber disposed within the body and comprising a filler material chosen from at least one of water, aphrons, water with solid particles suspended, and oil with particles suspended.

An earplug system is also provided by embodiments of the invention and can comprise: a user controllable pump; a stent with a fluid passageway disposed lengthwise therethrough and having a fluid inlet and a fluid outlet; a balloon in operable communication with the stent; wherein during use the balloon is inflatable with fluid by activating the pump to increase or decrease the amount of fluid in the balloon or to alter the composition of the fluid in the balloon.

Such earplug systems can further comprise a sound pathway duct disposed lengthwise through the stent.

Preferred embodiments of the invention provide an earplug comprising: a reservoir, where the reservoir includes a flowable medium; a valve; a channel; and a flexible distal end, where the reservoir is operationally connected to the distal end by the channel, where the valve is placed in the channel between the reservoir and the distal end, where the valve is configured to allow the medium to flow from the reservoir to the distal end, where the flowable medium is selected to attenuate at least one acoustic frequency within a first acoustic frequency bandwidth, and where an operational pressure of the flowable medium is selected to be within a pressure range during use. The operational pressure in the context of this specification refers to the pressure(s) at which the fluid within the device or system operates to achieve a desired attenuation result.

Such systems and devices can further comprise: a safety limiter flange, where the safety limiter flange diameter is designed to limit earplug insertion into the ear canal beyond a designed distance.

Even further, such systems and devices according to embodiments of the invention can comprise a distal end flange, where the distal end flange is expandable when the flexible distal end is expanded.

As an example, the first acoustic frequency bandwidth of such devices and systems can be between 250 Hz to 4000 Hz, and have a pressure range between 100 mbar and 1000 mbar gauge pressure.

Further, for example, the devices and systems can be configured such that the transmitted acoustic spectrum is flat across the first acoustic frequency bandwidth within about +/−5 dB.

More specific embodiments of the invention include an earplug with the medium being at least one of air, liquid, foam, water, oil, water with a salt, water with alcohol, alcohol, water with oil, aphrons, oil with suspended particles, water with suspended solid particles, water with suspended gelatinous particles, water and sugar, liquid with gas bubbles, and carbonated water.

Such inventive devices and systems can further comprise: a first movable element; and a second movable element, where the first and second moveable elements are configured to be moved by a user's fingers, where movement of the first and second moveable elements compress the reservoir, where upon compression the medium flows through the valve into the distal end where the valve restricts flow back to the reservoir.

Additionally, the earplugs can further comprise a release mechanism, where the release mechanism is configured to be operated by a user to allow medium to flow from the distal end to the reservoir.

Further preferred according to embodiments of the invention is an earplug comprising: a reservoir; and a medium, where the medium is contained within the reservoir, where the reservoir is deformable, and where the reservoir is configured to be compressed by a user's fingers and inserted into an ear canal, where the reservoir is configured to expand after being compressed by a user's fingers. Such devices and systems can be configured to comprise a finger tab or stem, where the finger tab or stem is configured to allow gripping of the tab with at least two fingers, where a user can pull on the tab to extract the earplug from the ear canal. More specifically, such earplug devices of the invention can contain a medium that is at least one of air, liquid, foam, water, oil, water with a salt, water with alcohol, alcohol, water with oil, aphrons, oil with suspended particles, water with suspended solid particles, water with suspended gelatinous particles, water and sugar, liquid with gas bubbles, and carbonated water.

The invention is not limited to devices and systems for the ear and other embodiments include an acoustic shaping panel comprising: a front; a back; a rim; and a medium container, where the medium container contains a medium, where the front, back, and rim substantially encloses the container, where the medium is selected to shape an incident acoustic spectrum to a designed transmitted acoustic spectrum.

Such acoustic shaping panels can be configured such that the transmitted acoustic spectrum is flat across the spectrum within about +/−5 dB from 250 Hz to 4000 Hz.

Further, the acoustic shaping panel can be configured to provide the medium at an operational pressure during use that is within a pressure range, such as from 200 mbar to 2000 mbar gauge pressure.

The acoustic shaping panels according to embodiments of the invention can comprise as medium at least one of air, liquid, foam, water, oil, water with a salt, water with alcohol, alcohol, water with oil, aphrons, oil with suspended particles, water with suspended solid particles, water with suspended gelatinous particles, water and sugar, liquid with gas bubbles, and carbonated water. The acoustic panels can be configured for use as a liner which, where the liner is configured to be inserted into the inside of a helmet.

In specific embodiments, the fluid medium of the acoustic panel is capable of reducing the amplitude of transmitted acoustic spectrum above 500 Hz by at least 15 dB from the incident acoustic spectrum. Even further, the acoustic panel according to embodiments can be configured such that the transmitted acoustic spectrum is flat across the spectrum within about +/−5 dB from 250 Hz to 4000 Hz.

Embodiments of the invention are capable of exhibiting an attenuation profile that is relatively flat across frequencies. In the context of this specification, "attenuation" is defined as the decrease in amplitude of a sound. It is most commonly measured as "insertion loss" wherein the sound is measured at the same exact point in the ear canal both with and without the hearing device or protector in place, and the difference in sound pressure level in decibels between those two measurements is taken to be the attenuation of the device. The measurements can be obtained by microphone in the ear, or by a human listener who listens for the sound at its hearing threshold, both with and without the device or protector in place. Further, the term "flat" may also be referred to as "uniform" and is intended to mean a small difference in attenuation across a range of frequencies.

For example, methods, systems, and devices of the present invention may exhibit an attenuation profile, which is flat, differing no more than 20 dB across a range of frequencies from 20 to 20,000 Hz. It may be desired to configure a particular device to have a specific attenuation profile over any bandwidth of frequencies, including for example at 125-8,000 Hz, a change such as less than 15 dB, or less than 10 dB, or less than 5 dB, or less than 2 dB across that range or any smaller range thereof. These flat profiles can also be present in smaller frequency ranges, such as from about 125-250 Hz, or from about 250-500 Hz, or from about 500-1,000 Hz, or from about 1,000-2,000 Hz, or from about 2,000-4,000 Hz, or from about 4,000-8,000 Hz, and so on. In embodiments, a first acoustic frequency, a second acoustic frequency, or any number of acoustic frequencies can be targeted by a particular device. More specifically, for example, devices, methods, and systems of the invention can exhibit an attenuation profile where the attenuation differs no more than about 5 dB from 4,000-8,000 Hz, or from 2,000-4,000 Hz, or from 1,000-2,000 Hz, or from 250-1,000 Hz, or from 250-500 Hz, or any combination thereof. Each of the aforementioned example ranges are exemplary of spectral adjustment or "tuning" with the invention. In the context of this specification, the terms bandwidth, frequency bandwidth, acoustic frequency bandwidth, and frequency range are intended to be interchangeable.

Objects of the invention further provide an earplug comprising: a balloon; a pump insert port operably configured to attach to a detachable pump system in a manner to pump fluid into the balloon from the pump when activated; a pump seal valve operably configured to close when the pump system is detached from the pump insert port. Such earplugs can comprise means for altering fluid composition.

Embodiments of the invention further provide earplug systems comprising: a first fluid reservoir; a second fluid reservoir; a lanyard or lanyard tube operatively connecting the first fluid reservoir and the second fluid reservoir; and a pump in operable communication with the lanyard tube, wherein the pump is capable of modifying fluid pressure in the first and second fluid reservoirs. In the context of this specification, the term lanyard or lanyard tube is intended to refer generally to a passageway for containing fluid. The passageway in embodiments is a hollow tube, which is preferably cylindrical.

Further embodiments include an earplug comprising: a stent with a fluid passageway disposed lengthwise therethrough and having a fluid inlet and a fluid outlet; a balloon disposed at a distal lengthwise end of the stent and in operable communication with the fluid outlet in a manner to receive fluid from the stent; a second balloon disposed at a proximal lengthwise end of the stent and in operable communication with the fluid inlet; a housing disposed at the proximal end of the stent and encompassing the fluid inlet and the second balloon, wherein the housing comprises a hollow cylindrical interior portion with a threaded interior surface; and a plunger for depressing the second balloon in a manner to push fluid from the second balloon into the first balloon, wherein the plunger comprises a disk-shaped head threaded around its circumference in a manner to engage with the threaded interior surface of the housing; wherein during use the plunger is capable of being rotated within the housing to depress the second balloon and produce a pressure to inflate the first balloon, or is capable of being counter-rotated to release depression of the second balloon and deflate the first balloon.

Preferred embodiments include earplugs wherein the fluid is air and the pressure is about 400 mbar to obtain a flatter attenuation profile between acoustic frequencies of about 125 Hz and about 8 kHz than with a lower pressure.

Also included within the scope of the invention is an earplug comprising: a body of compressible/expandable-recovery material shaped and sized to fit in an ear canal; and at least one chamber disposed within the body and comprising a filler material chosen from at least one of water, aphrons, water with solid particles suspended, and oil with particles suspended.

BRIEF DESCRIPTION OF THE DRAWINGS

The accompanying drawings illustrate certain aspects of some embodiments of the present invention, and should not be used to limit or define the invention. Together with the written description the drawings serve to explain certain principles of the invention.

FIGS. 1A and 1B are schematic diagrams illustrating the operation of at least one exemplary embodiment.

FIG. 5 is a schematic drawing illustrating a cartilaginous region and a bony region of an ear canal.

FIG. 6 is a schematic drawing illustrating general physiology of an ear.

FIG. 27 is a schematic diagram illustrating an acoustic shaping panel in accordance with at least one exemplary embodiment.

FIG. 28 is a schematic diagram illustrating a cross section of the panel illustrated in FIG. 27.

FIG. 29 is a schematic diagram illustrating attachment of the panels of FIG. 27 on a wall in accordance with at least one exemplary embodiment.

FIG. 30A is a schematic diagram illustrating the cross section of an acoustic shaping panel in accordance with at least one exemplary embodiment.

FIG. 30B is a schematic diagram illustrating a close-up of the medium illustrated in FIG. 30A.

FIGS. 31A, 31B, 31C, and 31D are schematic diagrams illustrating variations of cross sections of acoustic shaping panels in accordance with various exemplary embodiments.

FIGS. 32A, 32B, and 32C are schematic diagrams illustrating the configuration and operation of at least one exemplary embodiment.

FIG. 33 is a schematic diagram illustrating an earplug in accordance with one exemplary embodiment.

FIGS. 34A, 34B, and 34C are schematic diagrams illustrating the configuration and operation of at least one exemplary embodiment.

FIGS. 35A, 35B, 35C, and 36 are schematic diagrams illustrating the configuration and operation of at least one exemplary embodiment.

FIGS. 37 and 38 are schematic diagrams illustrating a helmet with a liner in accordance with at least one exemplary embodiment.

DETAILED DESCRIPTION OF VARIOUS EMBODIMENTS OF THE INVENTION

Figure 2:
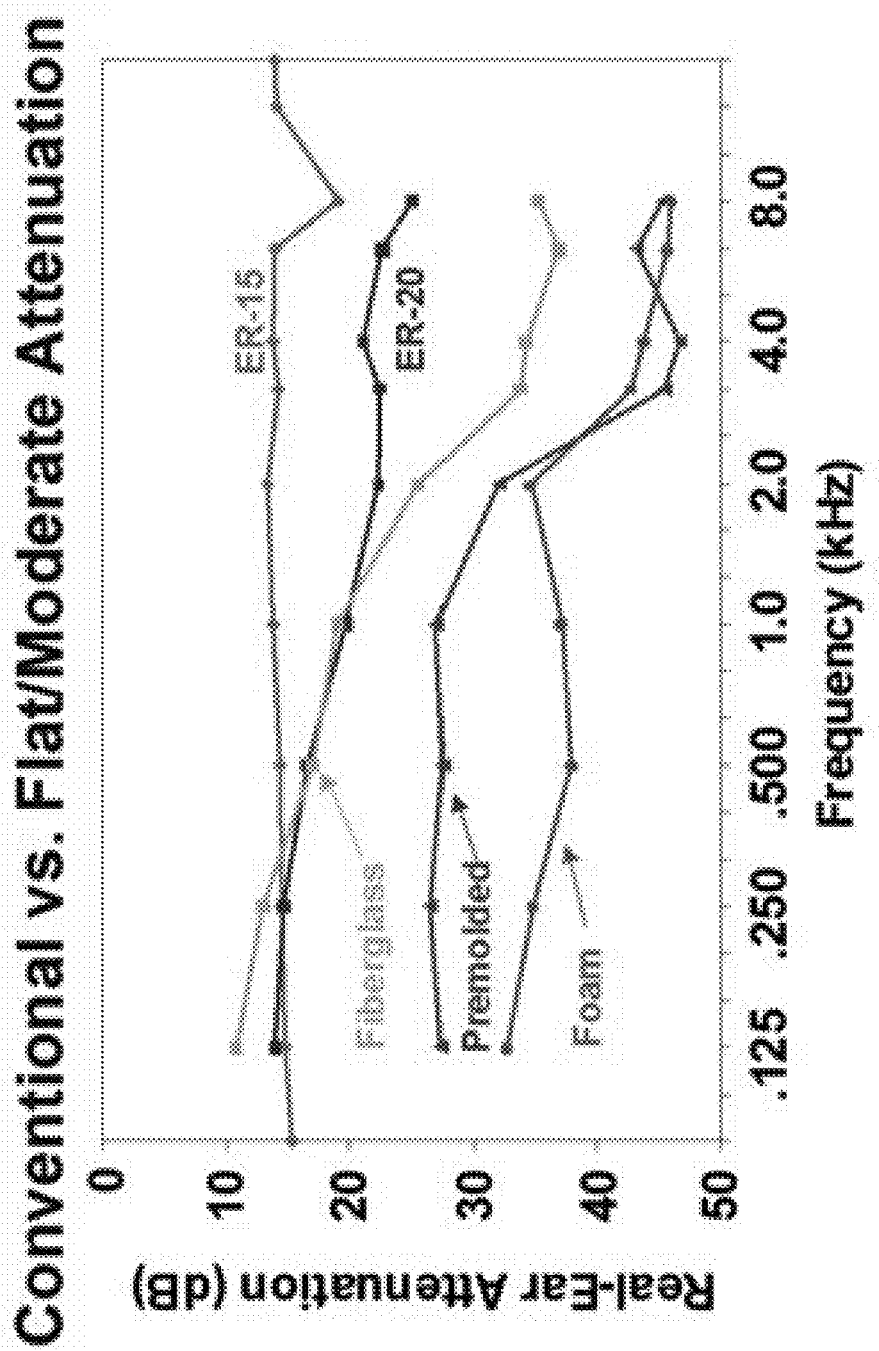
FIG. 2 is a graph of the attenuation profiles for various hearing protection devices across a range of frequencies from 125-8,000 Hz.
Figure 3B:
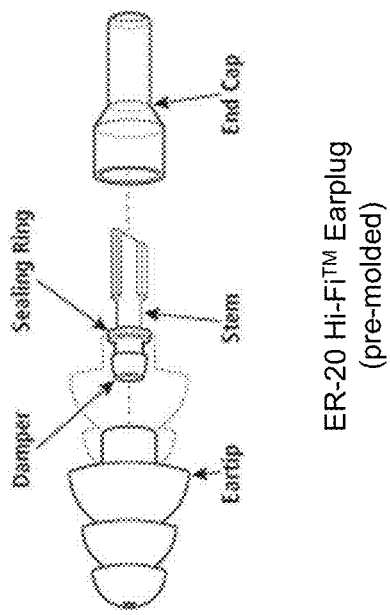
FIG. 3B is a schematic diagram showing an ER-20™ brand earplug.
Figure 3A:
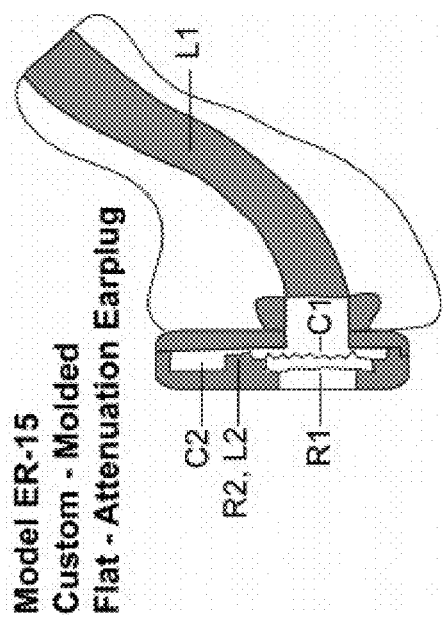
FIG. 3A is a schematic showing an ER-15™ brand musician's earplug.
Figure 4B:
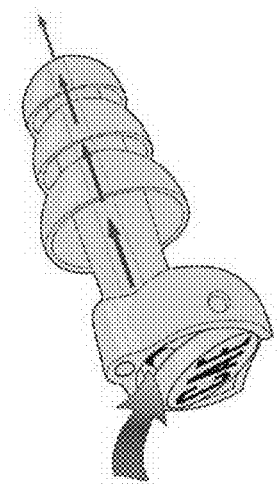
FIG. 4B is a schematic diagram of the third generation Combat Arms™ brand single-ended earplug.
Figure 4A:
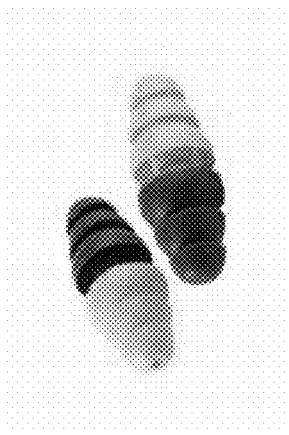
FIG. 4A is a schematic diagram of the first generation Combat Arms™ brand double-ended earplug.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Processes, techniques, apparatus, and materials as known by one of ordinary skill in the art may not be discussed in detail but are intended to be part of the enabling description where appropriate. For example, specific materials may not be listed for achieving each of the targeted properties discussed, however, one of ordinary skill in the art would be able, without undo experimentation, to determine the materials needed given the enabling disclosure herein.

It is noted that similar reference numerals and letters may be used to refer to similar items in multiple figures. Thus, once an item is defined in one figure, it may or may not be discussed or further defined in the following figures.

Exemplary embodiments are directed to or can be operatively used on various passive earplugs for hearing protection or electronic wired or wireless earpiece devices (e.g., hearing aids, ear monitors, earbuds, headphones, ear terminal, behind the ear devices or other acoustic devices as known by one of ordinary skill, and equivalents). For example, the earpieces can be without transducers (for a noise attenuation application in a passive hearing protective earplug) or one or more transducers (e.g., ambient sound microphone (ASM), ear canal microphone (ECM), ear canal receiver (ECR)) for monitoring/providing sound. In the examples illustrated and discussed herein, any specific values should be interpreted to be illustrative only and non-limiting. Thus, other examples of the exemplary embodiments could have different values.

FIGS. 1A and 1B illustrate the operation of at least one exemplary embodiment. Note that materials used for construction of earplugs, hearing aids, headphones, balloons and membranes can be used to construct exemplary embodiments used as earplugs. The device includes a reservoir 10, a fluid channel 40, a valve 20 and expandable element 30. The reservoir 10 includes a medium that can be tailored to vary the acoustic spectrum as a function of frequency. The distal end (right end of FIG. 1A) is inserted into an ear canal. The user then depresses Y1 the reservoir 10, which moves fluid from the reservoir 10 through the fluid channel 40 in a single direction as provided by the one way valve 20. The fluid movement into the expandable element 30 expands (Z1) the element 30 to a desired extent. The modification of any acoustic spectrum that passes through the earplug can be tailored (acoustically shaped) by varying the medium and pressure. Various non-limiting examples of various mediums will be discussed below, but in general can include liquids, gases, mixtures, colloidal suspensions, foams, gels, and particle suspensions. For example a colloidal suspension (e.g. aphron) can be held in suspension until mixed by a user (e.g., reservoir 10 squeezed) and a chemical reaction can occur (e.g., to generate heat to warm an earplug before insertion in cold climates).

Referring now to FIG. 5, this schematic diagram illustrates a generic cross section of an ear canal 100, including a cartilaginous region 140 and a bony region 130 of an ear canal 120. The entrance of the ear canal 120 is referred to as the aperture 150 and defines a first end of the ear canal while the tympanic membrane 110 defines the other end of the ear canal 120. The cross-area of the ear canal from the aperture to the tympanic membrane 110 is not uniform and changes in value. The cross-sectional area varies per person, making the development of an earplug that fits most, a difficult proposition.

FIG. 6 illustrates general outer physiology of an ear, which includes auricle tubercle 210, antihelix 220, helix 230, antitragus 240, tragus 250, lobule of ear 260, crus of helix 270, anterior notch 280, and intertragic incisures 290.

Figure 7:
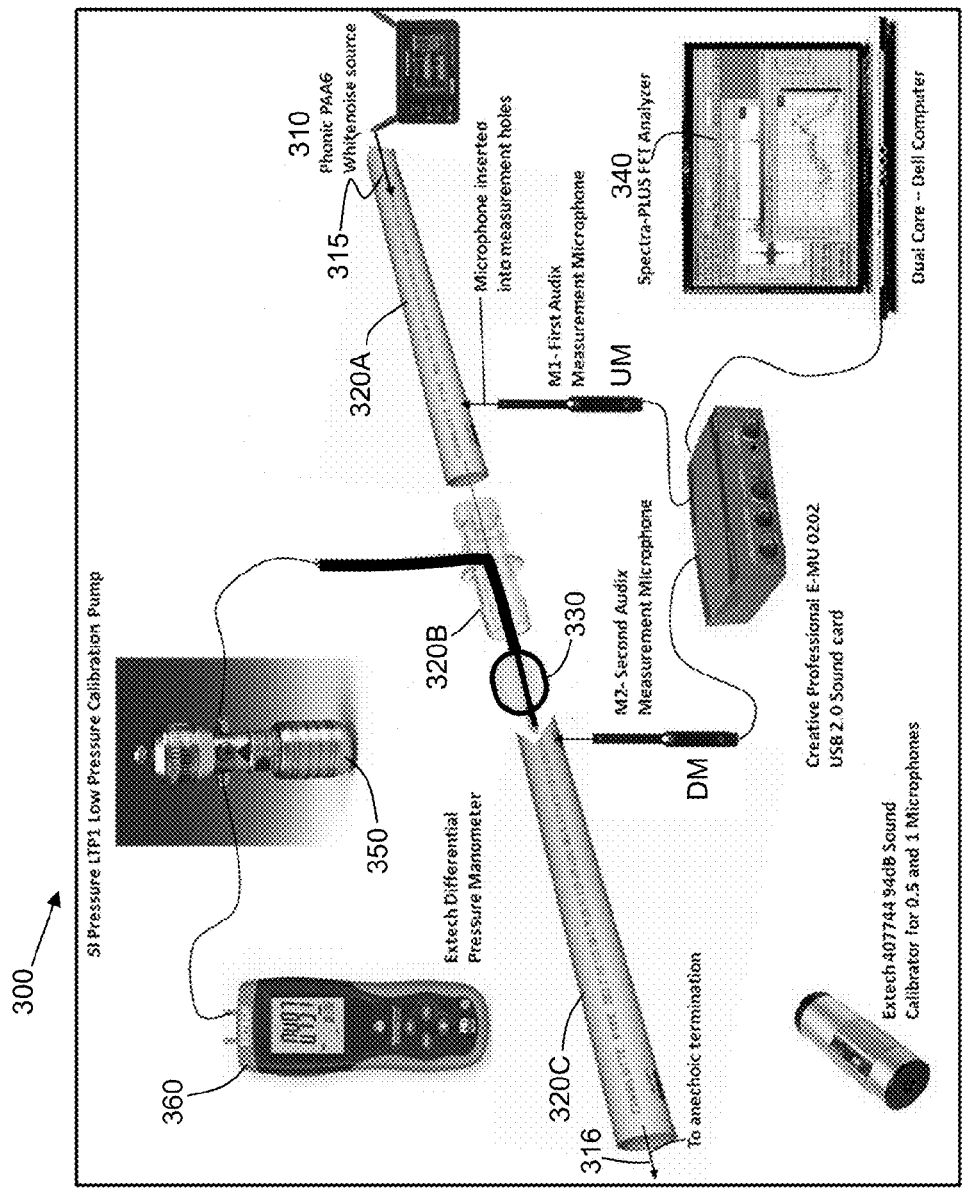
FIG. 7 is a schematic drawing illustrating a non-limiting example of an experiment for determining material properties of inflatable elements.

FIG. 7 illustrates a non-limiting example of an experiment for determining material properties of fillable elements. To isolate the variations in ear canal lengths, ear canal cross sections and insertion depths of earpieces (e.g., earplugs, in-the-canal hearing aids) an experimental setup 300 was constructed as illustrated in FIG. 7.

Generally, a noise source 310 (e.g., Phonic PAA6) generates acoustic source waves 315 (e.g., pink noise, white noise) which travel down an acoustic tube 320A where the incident acoustic signal is measured by an upstream first microphone (e.g., M1 or UM, Audix Measurement Microphone). The fillable elements 330 (e.g., hollow chamber such as a balloon in which various media or media combinations can be inserted) can be filled with various fluids (e.g., oil, foam, liquid and foam, aphrons, air, water, water with agents) and inserted into a portion 320B of the tunnel such that the acoustic source waves impinge one side of the test sample, travels through the test sample, and exit the opposite or adjacent (not shown) side of the test sample, where a downstream microphone (e.g., M2 or DM) measures the exiting acoustic waves.

To minimize reflections from the end of the downstream tube the system is set to have an anechoically terminated end, which is accomplished by length (>75 ft) so as to gradually diminish the energy of the travelling wave 316 by way of wall interaction, and by having small strands of string near the end to absorb more of the energy in the wave. The data from the two microphones M1 and M2 are obtained to extract acoustical spectrum information (e.g., using FFT analyzer software such as 340 Spectra-PLUS™ FFT Analyzer).

As noted prior herein, the term "insertion loss" (IL) in the context of this specification is defined as the difference in sound pressure levels in decibels measured sequentially at the same point before and after insertion of the device. When measuring insertion loss, measurements are taken with M2 prior to insertion of a test sample, then a test sample inserted and measurements retaken with M2. Using the same sound source in both measurements, the difference in the two measurements is defined as insertion loss (IL), which is the most commonly-applied measurement of attenuation of an HPD (see Casali II, 2010). For discussion herein with regards to tunnel data IL is approximated when using balloons by a difference in the uninflated M2 measurements (i.e. pressure of 000 mbar gauge pressure) and an inflated M2 measurement. The pressure of a test sample is varied by use of a pressure pump 350 (e.g., SI Pressure LTP1™ Low Pressure Calibration Pump), and monitored by reading the pressure from a pressure gauge 360 (e.g., Extech™ Differential Pressure Manometer).

Figure 9:
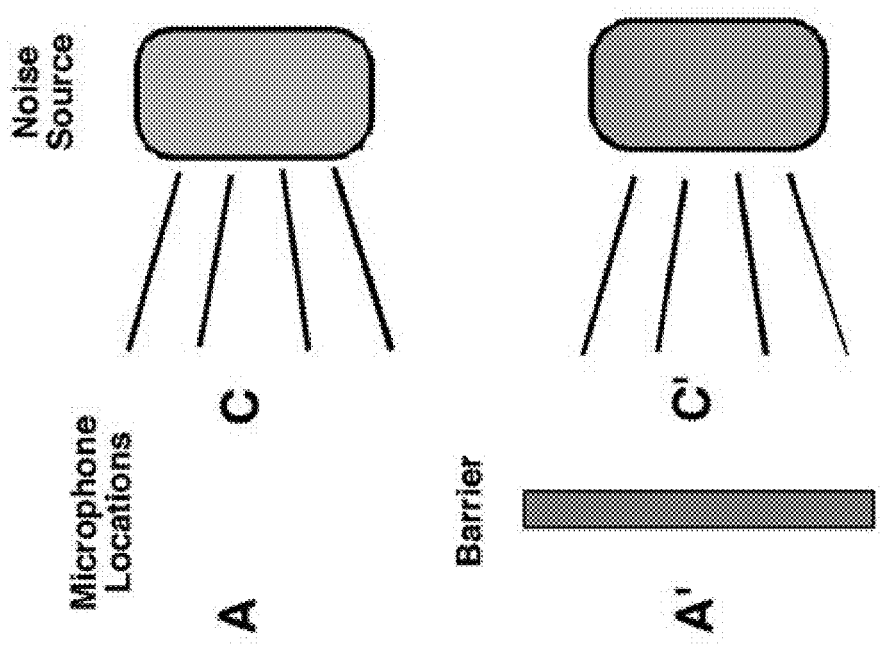
FIG. 9 is a schematic diagram illustrating an experimental set up for measuring insertion loss in a hearing protection device.

When HPD attenuation performance is quantified using microphone-based (i.e., physical) measurements, multiple approaches can be used, which may differ in the number of microphones and protocols used to perform the measurements, the locations of the microphones, and the time sequence of the measurements. As noted prior, for measuring insertion loss (IL) attenuation, a single stationary microphone is used and two measurements are performed, one with the HPD in place and one without the HPD present. For example, a schematic diagram is provided in FIG. 9, where the attenuation would be represented by the difference in the levels measured at A and A' (IL=A–A') (See Casali II 2010). The microphone can be located in an acoustical test fixture or in the concha or ear canal of a human test subject or acoustical manikin, or other comparable location.

Because real-ear threshold, i.e., listener-based, test procedures also represent two distinct threshold measurements performed at different times with and without an HPD in place, they can also be referred to as insertion loss measurements. Another protocol, noise reduction (NR), on the other hand, utilizes two microphones with the measurements made simultaneously on the interior and exterior of the HPD. Noise reduction is defined as the difference in sound pressure levels measured simultaneously at any two points along the path of sound propagation, i.e. inside the ear canal and outside of the ear canal for an external noise blocked by an earplug. NR would be represented by the difference in the levels measured at locations A' and C' in FIG. 9 (NR=C'–A'). (See Casali II 2010). As with insertion loss, NR measurements may be made using test fixtures, manikins, or human subjects. If human subjects are used, the measurements obtained at C' must be corrected for the transfer function of the open ear (TFOE) in the event that one wishes to calculate IL from the NR data. (Casali 2005; Perala, C. H. and Casali, J. G. Human subject investigation of MIRE microphone location during insertion loss testing of Active Noise Reduction hearing protectors in active and passive modes. Noise Control Engineering Journal, 57(5), 442-458, September-October, (2009) (Perala and Casali, 2009); Casali, J. G., Mauney, D. W., and Burks, J. A. Physical vs. psychophysical measurement of hearing protector attenuation—a.k.a. MIRE vs. REAT. Sound and Vibration, 29(7), 20-27. (1995), the disclosures of which are incorporated herein by reference in their entirety).

Most HPD attenuation data, at least for conventional HPDs, are obtained using human subjects in a binaural listening threshold shift methodology referred to as Real-Ear Attenuation at Threshold (REAT). As implemented in the old ANSI HPD test standard (ANSI S3.19-1974) that is currently required by the EPA, and in the recently proposed EPA rule that specifies ANSI S12.6-2008, subjects track their thresholds for ⅓-octave bands of noise with and without a hearing protector in place, these standards being incorporated by reference herein in their entireties. For S12.6-2008, these include bands with center frequencies of at least 125 Hz, 250 Hz, 500 Hz, 1000 Hz, 2000 Hz, 4000 Hz, and 8000 Hz. Again, the difference between the two thresholds (i.e., the threshold shift due to the difference in hearing thresholds with and without the presence of the HPD) at each ⅓-octave band represents the insertion loss attenuation of the hearing protector.

The REAT methodology is recognized as the most accurate method available in that it can account for individual differences in the fit of the devices across the subject sample as well as the human bone/tissue conduction effect, which, as a flanking path, constitutes the ultimate limiting factor in HPD attenuation. (See Perala and Casali, 2009) However, there are also disadvantages associated with REAT, including: overestimation of the low-frequency attenuation of devices due to physiological noise (due to the fact that the HPD enhances low frequency bone conduction, resulting in inflated occluded thresholds); inter- and intra-subject variability; and the need for extremely quiet test environments. It is important to note, however, that in the EPA's recently proposed rule, the EPA requires a REAT test per ANSI S12.6-2008 as a basis for labeling the passive attenuation of the device for all types of HPDs.

Figure 8:
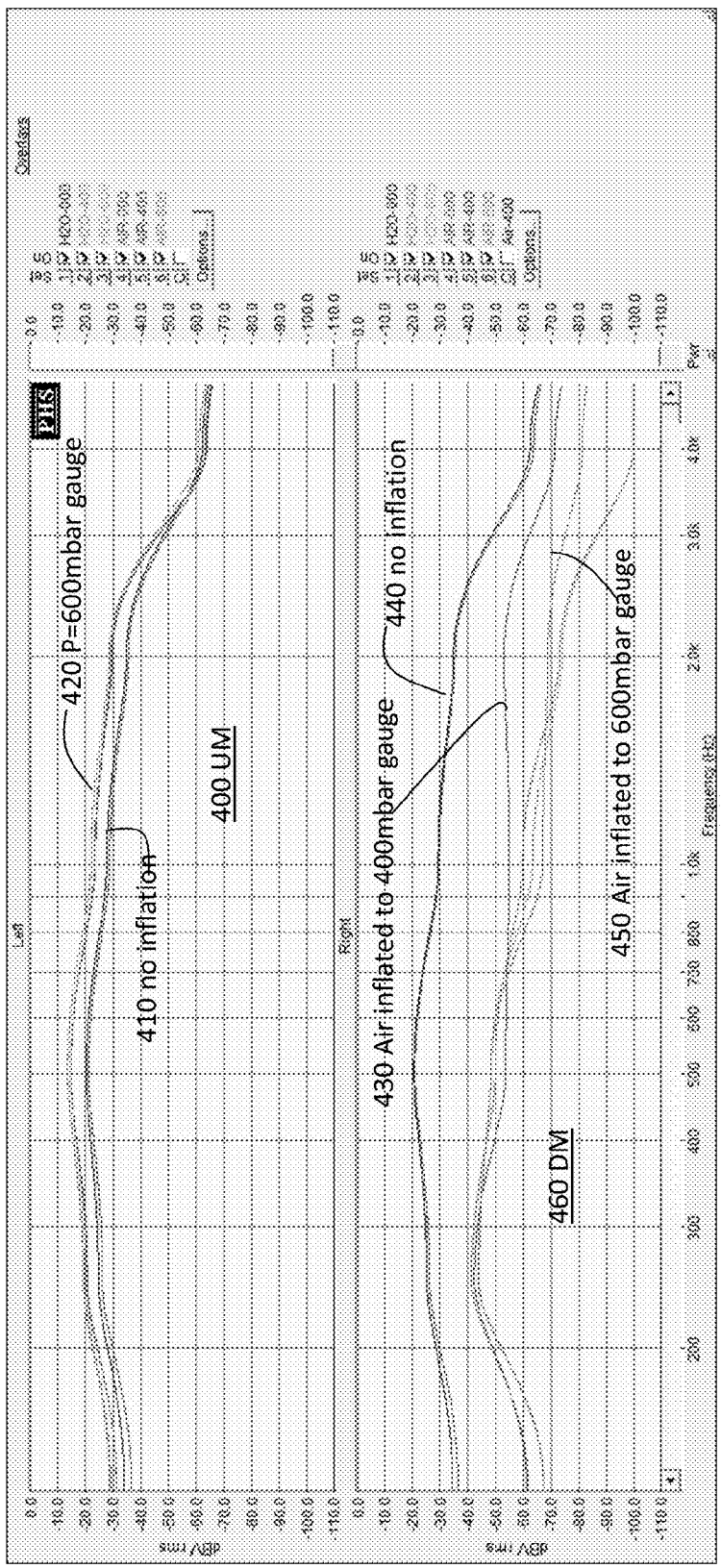
FIG. 8 is a graph illustrating the sound pressure levels (SPL) of the upstream microphone (UM) and the downstream microphone (DM) as a function of medium and pressure.

FIG. 8 illustrates the sound pressure levels (SPL) of the upstream microphone (UM) and the downstream microphone (DM) as a function of medium and pressure. Decibel (dB) Values rms between water and air at 000 mbar, 400 mbar, and 600 mbar gauge pressure are illustrated in FIG. 8. The term "rms" in the context of this specification means root mean square, a type of averaging for a waveform signal which varies over time and which is calculated by taking each value obtained, squaring each one, then taking the mean of all of the squares, then taking the square root of the result.

A larger decibel value indicates higher SPL values, thus a value of –10 dB is an increase of 20 dB in SPL value from –30 dB. Note that the values for 000 mbar represent the uninflated value and the insertion loss (IL) can be obtained by subtracting the 000 mbar value from the pressure values for the downstream microphone (DM).

Figure 10:
FIG. 10 is a graph illustrating the insertion loss (IL) value for three mediums, NaCl, $H_2O$, and Air at 400 mbar gauge pressure.
Figure 16:
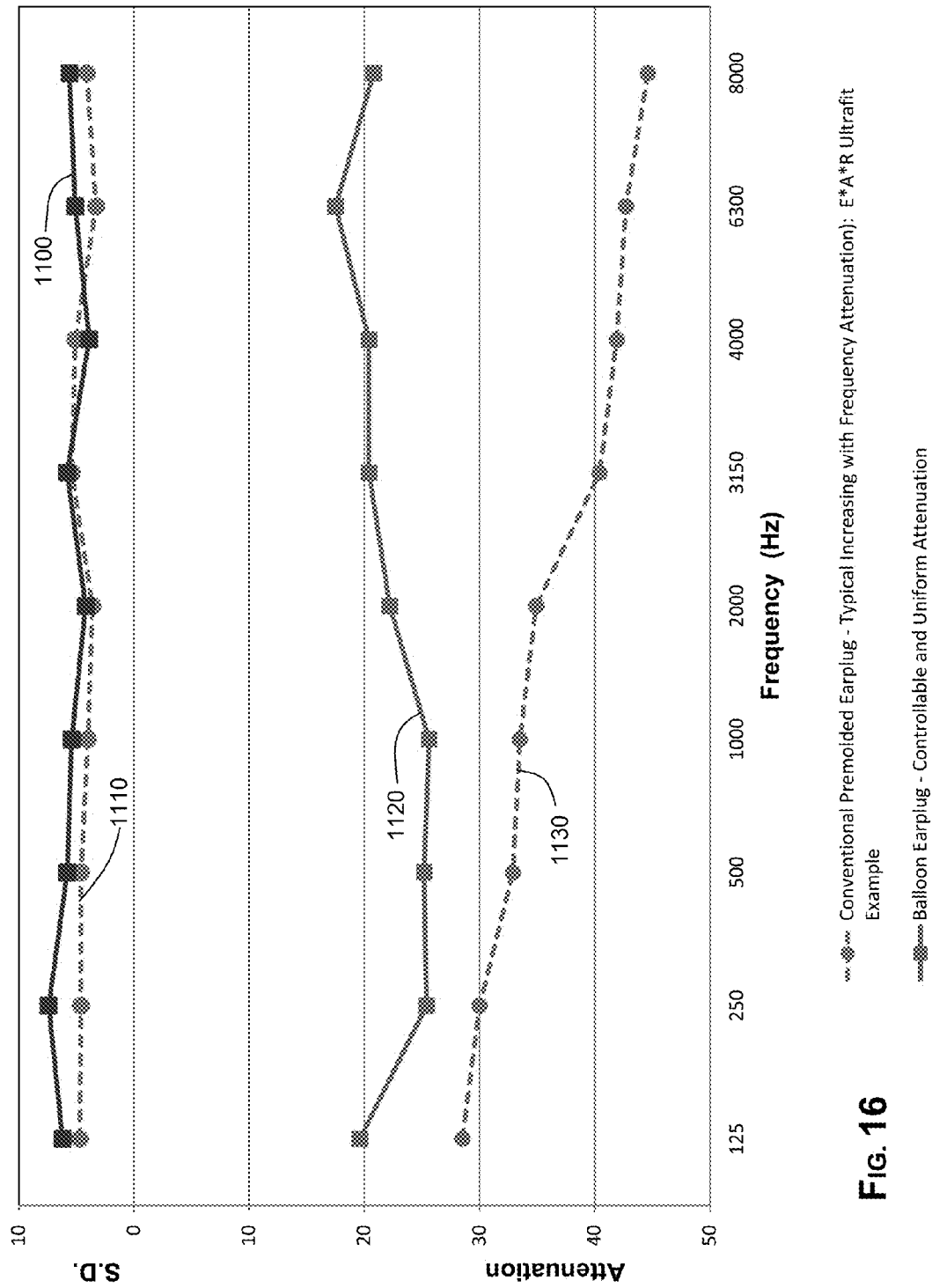
FIG. 16 is a graph illustrating a comparison of REAT values of attenuation and standard deviation for an inflatable passive earplug and a conventional, passive pre-molded earplug.
Figure 17:
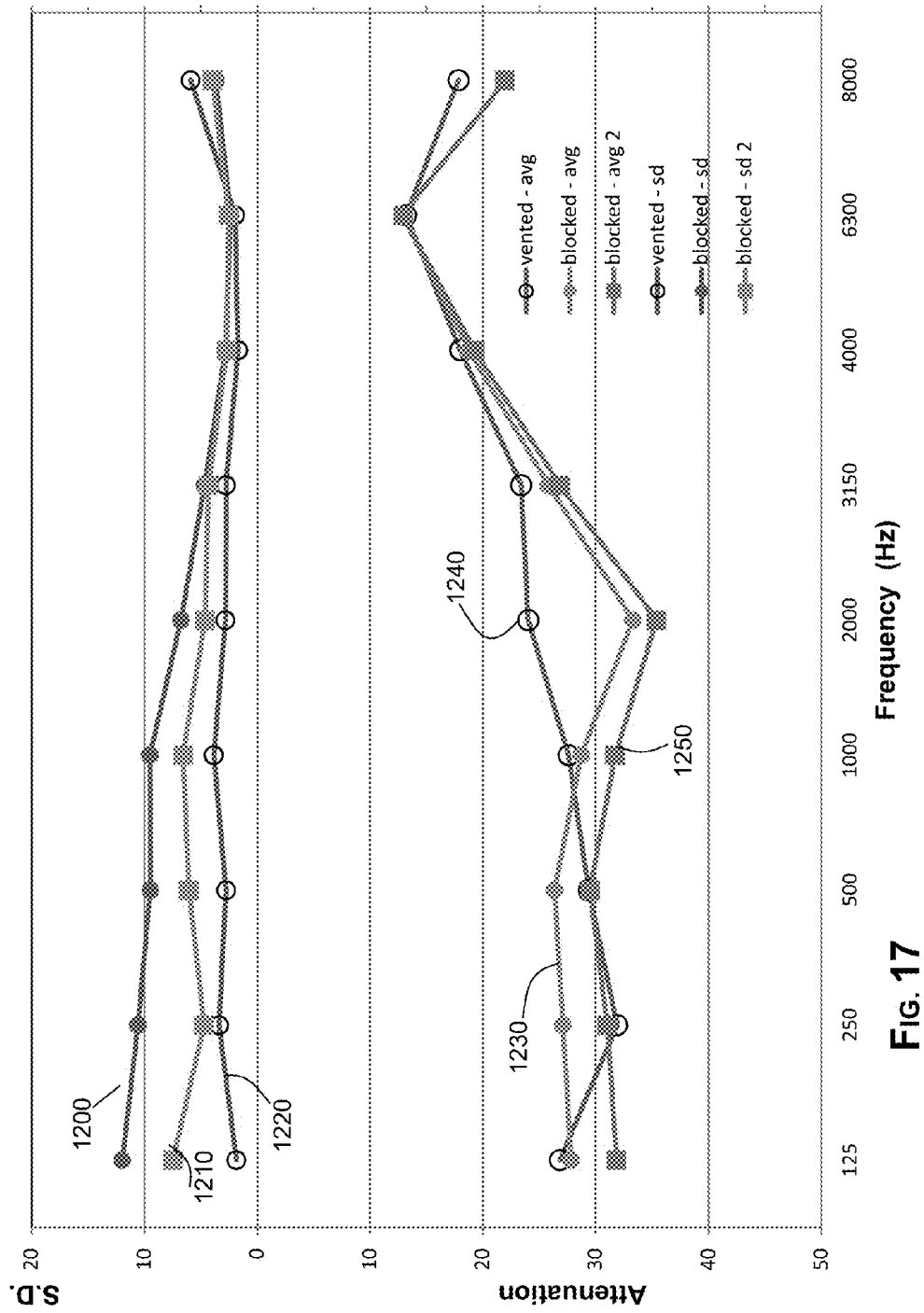
FIG. 17 is a graph illustrating comparison REAT values of attenuation and standard deviation for inflatable earplugs with and without vents.

Insertion loss (IL) values are presented in FIG. 10 and are obtained by taking the arithmetic difference at each specified frequency between measurements taken with and without the HPD in place. Possible measurements can be made at the ear canal, both unoccluded and occluded with external noise. For a hearing protector, the amount of sound pressure level (SPL) reduced, usually measured in decibels (dB), is typically depicted graphically as a function of frequency. Note also that the plotting values are 1-octave values and hence have been averaged from the narrowband data. Thus, details in the narrow band data are lost, however, the 1-octave values allow more direct comparison to human subject data (FIGS. 16 and 17).

Note that although FIG. 8 illustrates the use of air as an example, it is meant to be a non-limiting example and other mediums or combinations of mediums can be used. The flowable media, which includes fluids, is intended to mean any media capable of flowing when a pressure is exerted upon it.

For example, any fluid such as water, oil, or gas, or solids suspended in a fluid, or combinations thereof can be used. Gels can also be used as the medium, if desired. Aphrons dispersed in a foam-type medium, or other solid or semi-solid medium, are another option. Each medium can have a different effect on the insertion loss as a function of frequency. For example, using air as the medium, as the pressure increases the insertion loss also increases from about 700 Hz to 4.0 kHz. This is one example of spectral tuning.

The top panel of FIG. 8 illustrates upstream microphone 400 (UM) measurements under six conditions, water as the medium under three pressures: 000 mbar (blue), 400 mbar (green), and 600 mbar (light blue); and air as the medium under the same three pressures: 000 mbar (light purple), 400 mbar (red), and 600 mbar (orange). Note that the pressure conditions separate into two general separate lines, the first with no inflation for example 410, and a second line where the two non-zero pressure values generally overlap into a single line 420. Thus generally independent of pressure in the sample, an increase of about 7 dB is measured upstream of the test sample. One possible interpretation is that 7 dB of incident energy is reflected from the interface.

The bottom panel illustrates downstream microphone 460 (DM) measurements under six conditions, water as the medium under three pressures: 000 mbar (blue), 400 mbar (green), and 600 mbar (light blue); and air as the medium under the same three pressures: 000 mbar (light purple), 400 mbar (red), and 600 mbar (orange). Note that the pressure conditions separate into two general regions, the first region is associated with no inflation 440 where irrespective of medium, as one might expect, the lines overlap. The other region varies depending upon medium and pressure. For example, a red line marks dB values for air at 440 mbar and the orange line dB values for 600 mbar. In general as the pressure increases the rms dB value decreases in value as measured by DM. Note that between a frequency of 300-700 Hz an increase in pressure is not associated with a decrease measured value at DM. Note that both UM and DM measurements have roughly a frequency independent standard deviation of <0.2 dB.

FIG. 10 illustrates the insertion loss (IL) values 500 for three mediums, NaCl, $H_2O$, and Air at 400 mbar gauge pressure as measured by the downstream microphone DM. Note that a larger IL value is associated with more energy being removed from the initial acoustic wave by the test sample. As illustrated the three different mediums, distilled $H_2O$ with 1.95 mg/L NaCl (light blue line) 510, distilled $H_2O$ (blue) 520, and Air (red) 530, are distinguishable. For example air provides less IL after 700 Hz than $H_2O$ 520 and $H_2O$+NaCl mixture 510. Note that $H_2O$ 520 and $H_2O$+NaCl mixture 510 have similar profiles below 700 Hz and above 3 kHz. Between 700 Hz-3 KHz the IL values 510 and 520 differ such that an $H_2O$+NaCl mixture provides more IL. Note that although an $H_2O$+NaCl mixture is illustrated, other mixtures (e.g., with sucrose, alcohol, mineral oil, various other compound concentrations) can be used to tailor specific increases or decreases in IL as a function of frequency for a given pressure. For example if low frequency attenuation is needed below 700 Hz without significant attenuation above 700 Hz air can be used. If attenuation is desired above 700 Hz then $H_2O$ 520 or $H_2O$+NaCl 510 can be used. If flat attenuation is desired between 500 Hz to about 1000 Hz, $H_2O$ can be used as the filling medium. For example a foam plug with a hollowed-out center portion that is filled with fluid can be used.

Figure 11:
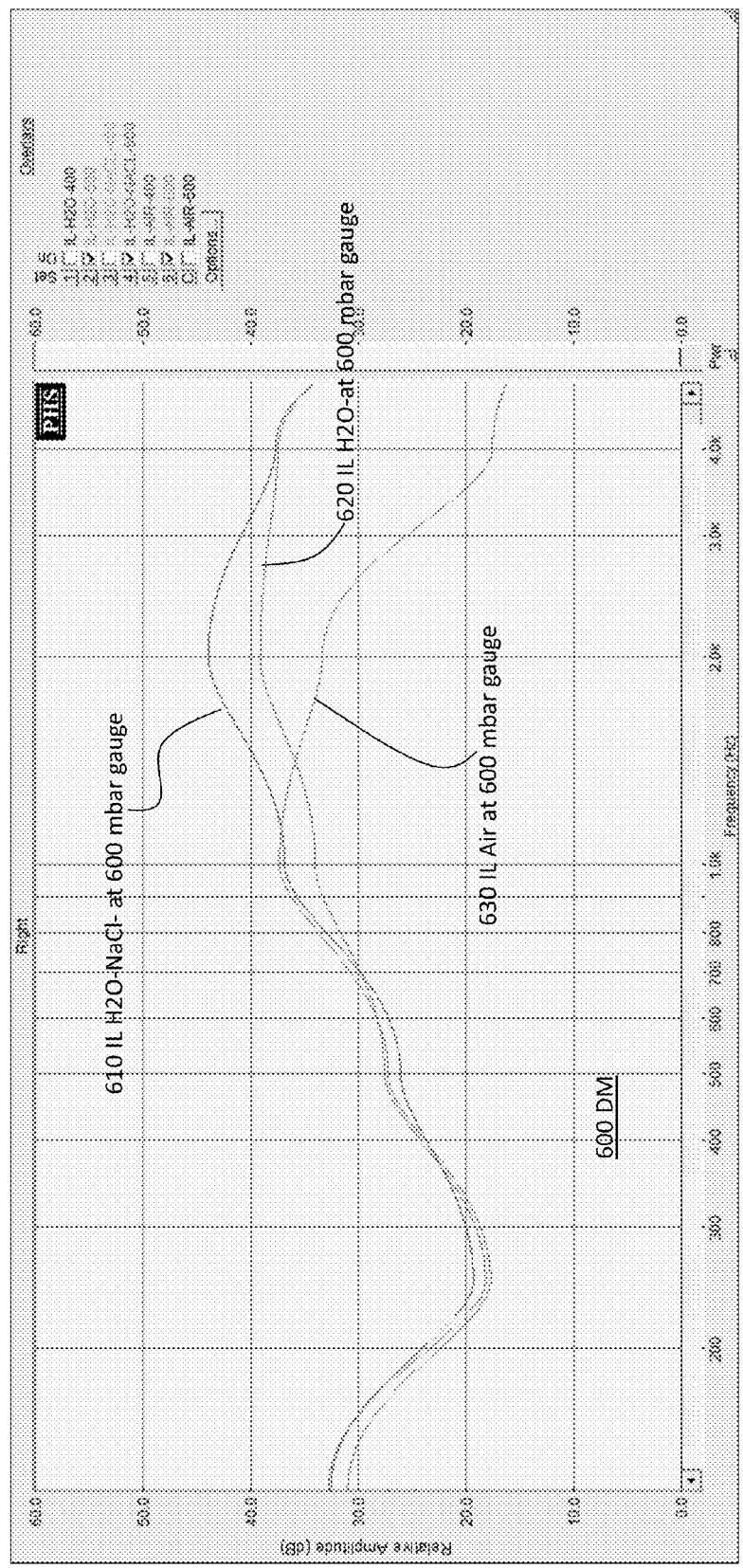
FIG. 11 is a graph illustrating the insertion loss (IL) value for three mediums, NaCl, $H_2O$, and Air at 600 mbar gauge pressure.

At higher pressures the $H_2O$, $H_2O$+NaCl, and Air have similar insertion losses up to higher frequencies as the pressure increases as seem in FIG. 11. Thus the attenuation properties can be modified as pressure is modified. FIG. 11 illustrates the insertion loss (IL) values 600 for three mediums, NaCl, $H_2O$, and Air at 600 mbar gauge pressure as measured by the downstream microphone DM. Note that a larger IL value is associated with more energy being removed from the initial acoustic wave by the test sample. As illustrated the three different mediums distilled $H_2O$ with 1.95 mg/L NaCl (light blue line) 610, distilled $H_2O$ (blue) 620, and Air (red) 630 are distinguishable. For example air provides less IL after about 1.5 kHz than $H_2O$ 620 and $H_2O$+NaCl mixture 610. Note that the decrease with air as a medium after 1.5 kHz differs from the 400 mbar value of 700 Hz. Thus at increased pressures air 630 provides less IL than $H_2O$ 620 and $H_2O$+NaCl mixture 610 above a higher frequency. Thus generally as the test sample pressure is increased, the IL profiles also vary, facilitating using controllable pressure values to obtain design IL profiles as well as using various medium filler. For example, if an earplug uses air and an IL value above 700 Hz in unimportant for the particular use, then an earplug can be designed to have an internal balloon or chamber pressure of about 400 mbar, whereas if the IL value above 1.5 kHz is unimportant then the earplug balloon can be designed to have an internal pressure of 600 mbar and/or a different medium than air.

Note that $H_2O$ 620 (green) and $H_2O$+NaCl mixture 610 (red) have similar profiles up to about 700 Hz. Above 700 Hz, the IL values 610 and 620 differ such that an $H_2O$+NaCl mixture provides more IL. Note that although an $H_2O$+NaCl mixture is illustrated, other mixtures (e.g., with sucrose, alcohol, mineral oil) can be used to tailor specific increases or decreases in IL as a function of frequency for a given pressure. Thus, if an earplug is designed for use with distilled water, the IL value can be varied at different frequencies by adding agents (e.g., NaCl). If one wishes to increase the IL above 700 Hz one could add a mixture of NaCl and distilled water 620.

Figure 12:
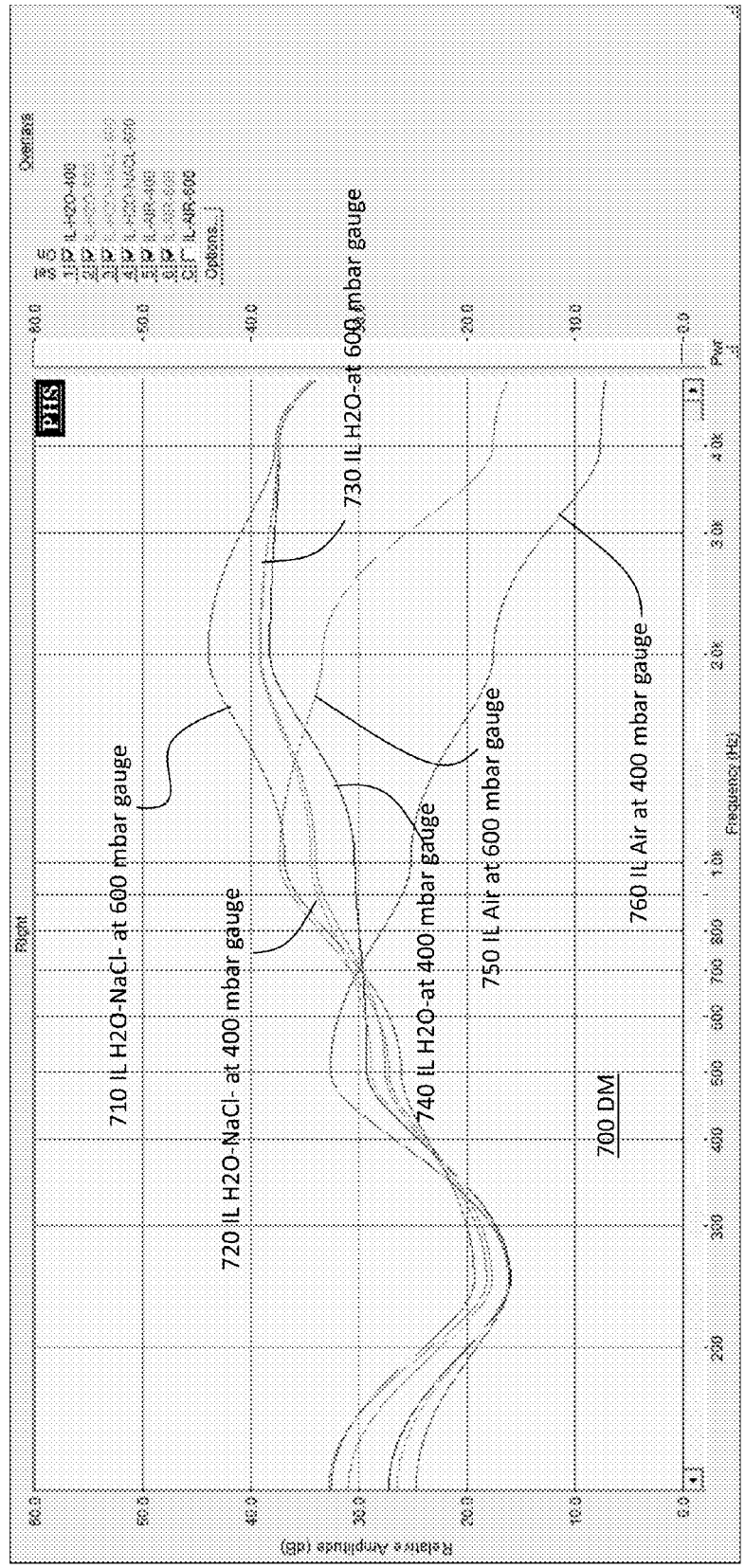
FIG. 12 is a graph illustrating the insertion loss (IL) value for three mediums, NaCl, $H_2O$, and Air for 400 mbar and 600 mbar gauge pressures.

FIG. 12 illustrates the insertion loss (IL) value 700 for three mediums, NaCl, $H_2O$, and Air for two pressures 400 mbar and 600 mbar gauge pressures as illustrated in FIGS. 5 and 6 for ease of comparison. Note that a fillable medium (e.g., NaCl) such as illustrated in FIG. 12, 710 results in an enhanced insertion loss above 700 Hz compared with water 730.

Figure 13:
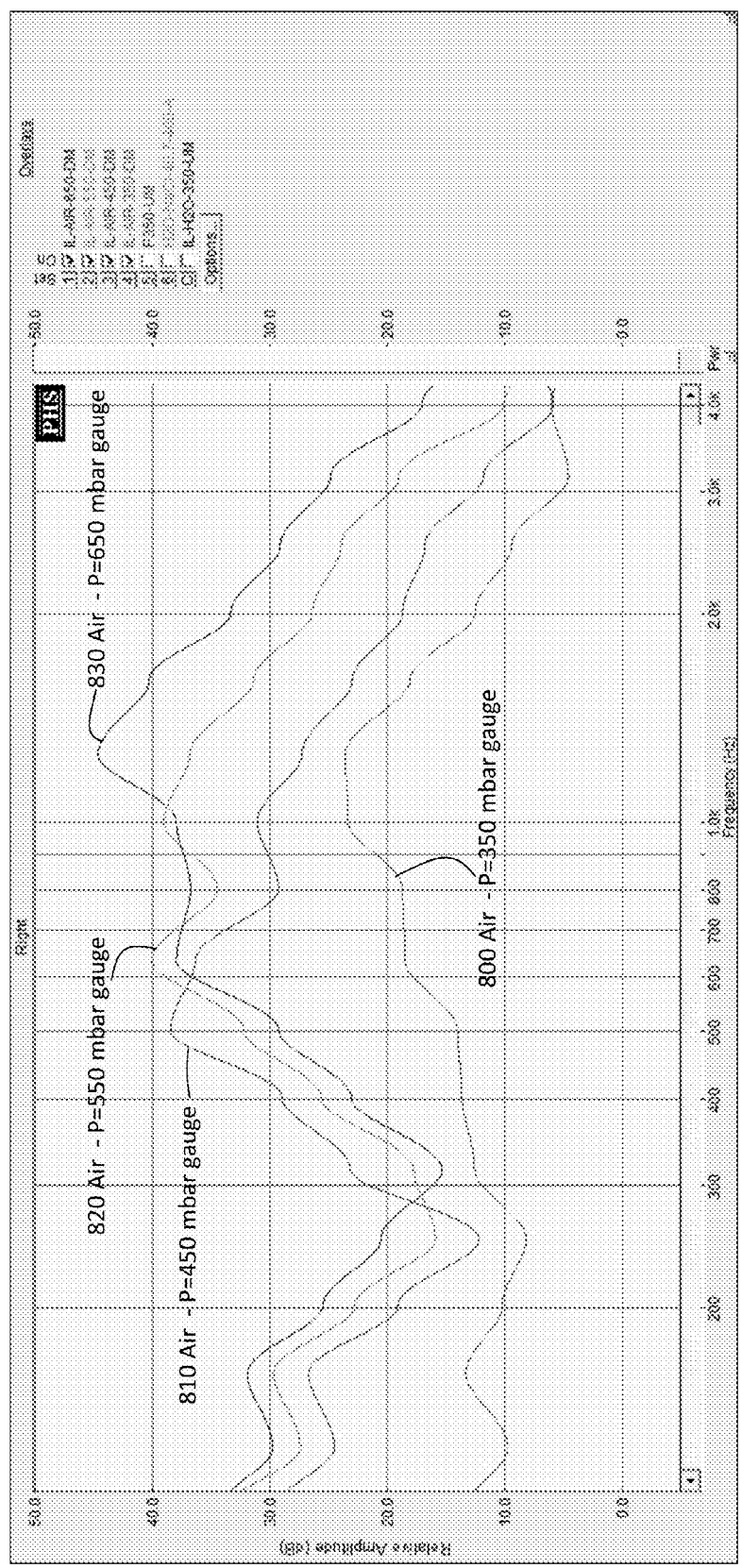
FIG. 13 is a graph illustrating insertion loss (IL) for Air for gauge pressures of 350 mbar, 450 mbar, 550 mbar, and 650 mbar gauge pressures.

FIG. 13 illustrates the insertion loss (IL) value for Air for gauge pressures of 350 mbar (800), 450 mbar (810), 550 mbar (820), and 650 mbar (830) gauge pressures. In general as the pressure of a test sample increases the IL value increases for frequencies less than about 300 Hz and greater than about 1 kHz. Between about 300 Hz and 1 kHz the pressure with the larger IL depends upon frequency. For example, a pressure of 450 mbar has a larger IL value than other pressures at about 500 Hz, while a pressure of 550 mbar has the largest IL value at about 650 Hz. Thus pressure can be varied in an earplug device to modify the frequency at which the greatest IL is provided. For example, suppose the frequency of an offending noise source gradually increases in frequency. An air-filled earplug with interactive pressure control could increase the pressure of an earplug balloon to maintain suppression of the noise source as its frequency increased. Notice that there is an attenuation increase as a function of pressure that is more pronounced for air (FIG. 13) than for the same pressures for water (FIG. 14).

Figure 14:
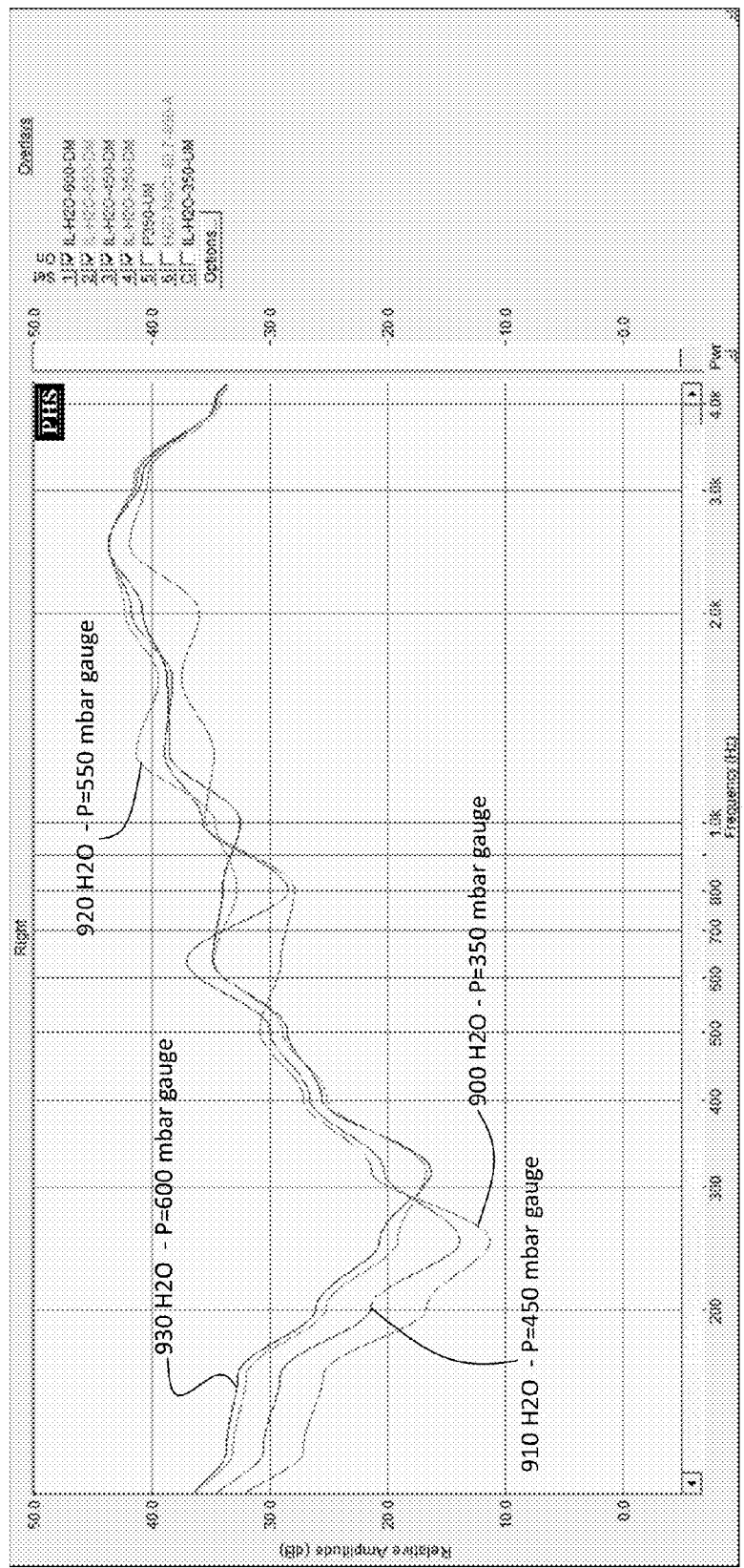
FIG. 14 is a graph illustrating insertion loss (IL) for $H_2O$ for gauge pressures of 350 mbar, 450 mbar, 550 mbar, and 600 mbar gauge pressures.

FIG. 14 illustrates the insertion loss (IL) value for $H_2O$ for gauge pressures of 350 mbar (900), 450 mbar (910), 550 mbar (920), and 600 mbar (930) gauge pressures. In general as the pressure of a test sample increases the IL value increases for frequencies less than about 300 Hz. Above about 300 Hz the pressure with the larger IL depends upon frequency. For example a pressure of 450 mbar has a larger IL value than other pressures at about 625 Hz, while a pressure of 550 mbar has the largest IL value at about 1.25 kHz. Thus pressure can be varied in an earplug device to modify the frequency at which the greatest IL is provided. For example, suppose a flatter frequency dependent IL is desired between frequencies of about 500 Hz and 800 Hz, then the pressure of an $H_2O$ filled earplug bladder can be set to about 350 mbar and if an increase of IL is needed within this range then the pressure can be increased.

Figure 15:
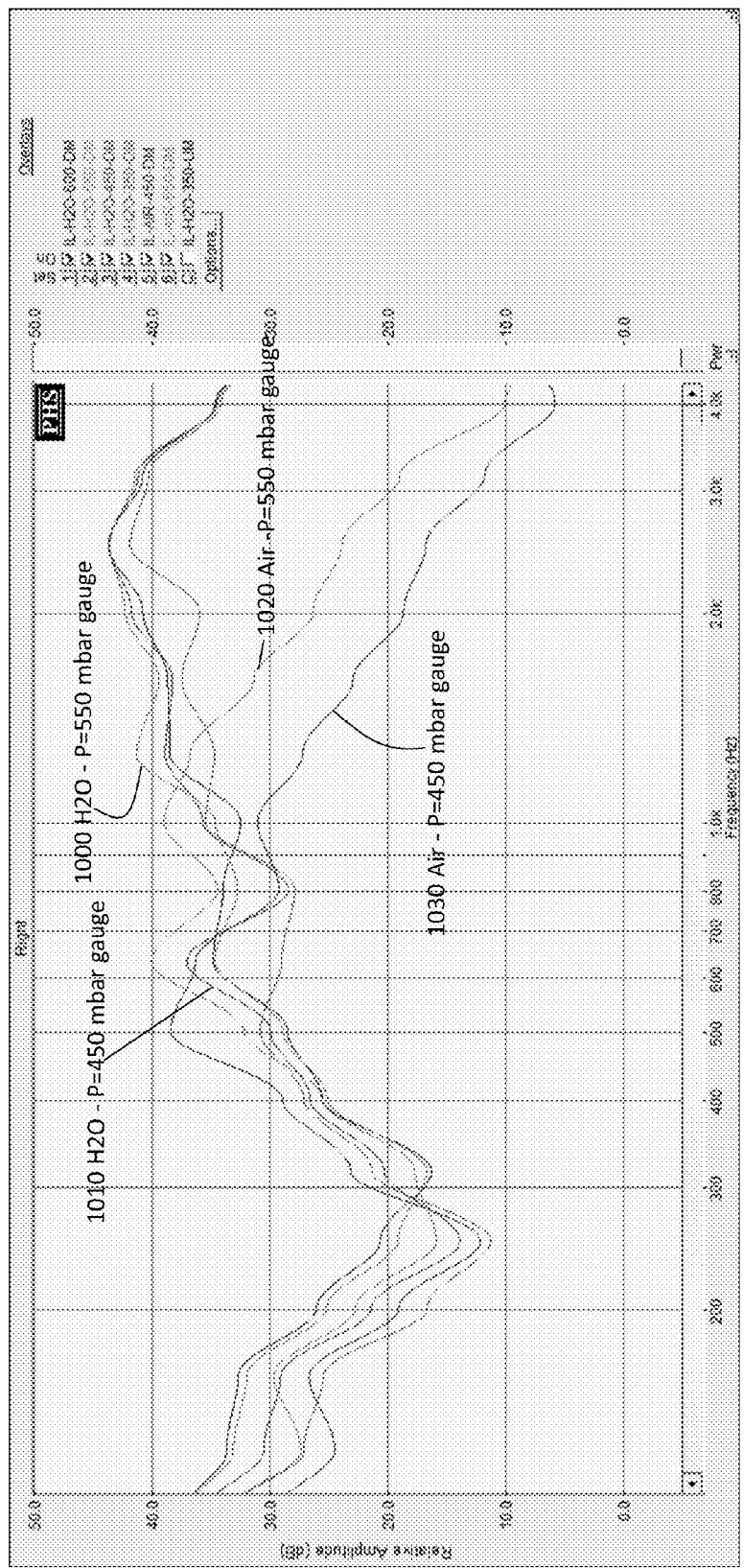
FIG. 15 is a graph illustrating the insertion loss (IL) value for two mediums, $H_2O$, and Air for 450 mbar and 550 mbar gauge pressures.

FIG. 15 illustrates the insertion loss (IL) value for the $H_2O$ values of FIG. 14 and two air values for comparison Air at 450 mbar (1030) and 550 mbar (1020) gauge pressures. Note that peak IL values differ from the fluid used (e.g., air or $H_2O$). For example, if an earplug device is designed to maximize IL at 500 Hz, then one can use air at 450 mbar, where if one wishes to maximize the IL at about 650 Hz the air pressure can be increased to 550 mbar. If one wishes to design an earplug to maximize IL at about 1.25 kHz then one can use $H_2O$ at a pressure of about 550 mbar. Note that a flatter IL profile when using $H_2O$ can be obtain between frequencies about 500 Hz and 1 kHz by setting the $H_2O$ pressure to about 550 mbar as opposed to 450 mbar. As stated earlier, the insertion loss attenuation test values noted above are from actual measurements in an acoustic tube system, and a person having ordinary skill in the art will recognize that while they do not substitute exactly for attenuation values measured by the much more lengthy human listener tests specified in the real-ear attenuation at threshold (REAT) standards (ANSI S3.19-1974; ANSI S12.6-2008), they do provide a reasonable approximation to REAT measurements at least to the point of rank-ordering spectral attenuation achieved using different filler media and pressures.

FIG. 16 illustrates a comparison of REAT values of attenuation and standard deviation for an inflatable earplug and a conventional premolded earplug. Conventional HPDs are, under the prevailing EPA regulation, tested for spectral attenuation at the threshold of hearing using a real-ear attenuation at threshold (REAT) standard (ANSI S3.19-1974; Experimenter-Fit Method); this standard proposed to soon to be replaced by ANSI S12.6-2008 in the EPA's newly proposed rule. (See Casali II, 2010) More specifically, in FIG. 16, attenuation versus frequency of an inflatable balloon-type earplug according to an exemplary embodiment of the invention is shown using the box-coded curve and is compared with that of the commercially-available premolded E•A•R/3M UltraFit™ earplug shown using the circle-coded curve (referring to the two lowermost mean attenuation curves). As illustrated, the inflatable earplug embodiment of the invention achieves the desired attenuation profile similar to the flat or uniform attenuation profile shown in FIG. 15, as compared to the highly-nonlinear and increasing—with frequency attenuation of the commercially-available conventional premolded E•A•R/3M UltraFit™ earplug. Thus, at least one exemplary embodiment of the present invention, in at least one of its embodiments as shown herein, achieves the near-flat attenuation profile that can be desirable for certain noise exposure protection situations. In fact, the attenuation spectrum in this example shows a flat profile that is limited to a narrow amplitude range of 6 dB (19.6-25.6) from 125 Hz to 8000 Hz, which is tighter (and thus flatter) than the 8.4 dB range (13.2-21.6) of the E•A•R/3M UltraFit™ earplug from 125 Hz to 8000 Hz (FIG. 16). This can be construed as a distinct design advantage of at least one exemplary embodiment of the present invention.

At least one exemplary embodiment does not rely on any multi-component, static mechanical configurations of the types used in the Etymotic Research, Inc. flat attenuation earplugs discussed on the Etymotic website. Instead, at least one exemplary embodiment of the present invention employs a simple stretch membrane (i.e., "balloon") approach, wherein an inflatable, lightweight balloon is inserted into the ear canal in its deflated state, and then inflated once inside the canal. Balloons can be either constant volume or variable volume. A constant volume balloon will not expand beyond predetermined dimension and additional air injection will mostly result in increased pressure. A variable volume balloon will continue to expand beyond initial inflation and it will deform to comply with the ear canal shape. Additional air injected into a variable volume balloon will result in increased volume and/or pressure. This insertion configuration affords its own additional advantages in the realm of having an in-ear product that is undersize compared to the diameter of the ear canal prior to insertion, and then expands once inside the canal, unlike most other earplug products on the market, including the Ety High Fidelity™ earplug from Etymotic Research, Inc., which are sized to be oversize the ear canal prior to insertion, and thus require some manual force to squeeze the flanges upon insertion, making insertion more difficult, and possibly causing slight pain in some individuals.

To achieve the attenuation shown in FIG. 16, the balloon-type earplug was inserted fully into the canal so that its outer end was at or near the aperture of the canal, and then it was inflated with air to a comfortable pressure of about 1.39-1.42 bar, resulting in the inflated state. Inflation and pressure maintenance during testing was performed with an apparatus similar to that shown in FIG. 7. Note that the pressure 1.39-1.42 bar absolute can be used to determine acceptable ear canal pressure exerted from a device. Attenuation measurements were made in accordance with the prevailing standard at the date of measurement, ANSI S3.19-1974, using 10 subjects and real-ear threshold testing in the hearing protector test facility of the Virginia Tech Auditory Systems Lab. This particular configuration of a single-bulb, variable volume, silicone medical balloon was tested at the aforementioned pressure range, with air as the filling medium, and with the pass-through vent in the balloon left open (i.e., not sealed off). Vents or ducts cut through an HPD or a hearing aid serve several functions: to reduce the occlusion effect and negative impact of hearing own voice as boomy or resonant, to improve the hearing of bass and the bass response of hearing aids, and to reduce any pressure felt when inserting the device. It comes at the cost of reducing the low-frequency protection (attenuation or insertion loss) of the device when the vent is open to the outside world. As discussed above, different balloon-fill fluid media (e.g., various liquids or gases), different inflation pressures, alternative vent configurations (e.g., closed as opposed to open vents, various diameter open vents, tortuous vs. straight path vents), different balloon types (e.g., multiple bulbs, constant volume as opposed to variable volumes), alternative balloon materials (e.g., silicone alternatives), and other changes to the basic embodiment discussed herein will produce different attenuation results and thus are important to the invention's overall scope and design latitude coverage. Nonetheless, the test results presented in FIG. 16 provide clear evidence that this invention produces flat attenuation within a narrow decibel range across one-third octave bands centered at 125, 250, 500, 1000, 2000, 3150, 4000, 6300, and 8000 Hz in the audible frequency bandwidth. Humans, at least those with young, normal ears, can hear sounds in the dynamic amplitude sensitivity range of about 0 to 120 dB and in the frequency sensitivity bandwidth of approximately 20 to 20,000 Hz. This ability to achieve a flat or near-flat attenuation spectrum is believed to be a primary benefit of the technology, for certain noise exposure and human listening situations.

FIG. 17 illustrates a comparison of REAT values of attenuation and standard deviation for an inflatable earplug with and without vents. The top panel illustrates the standard deviation values for three configurations. The fluid is air and the pressure is about 400 mbar gauge pressure. The three configurations 1230, 1240, and 1250 involve two designs, one with an open vent passing through the earplug (1240) and two non-vented (i.e., "solid" designs with no pass-through tube) (1230 and 1250). The vented design has an open tube before insertion passing through an inflation stent. The non-vented design is a sealed vent (tube) similar to that discussed in FIG. 18.

Figure 18:
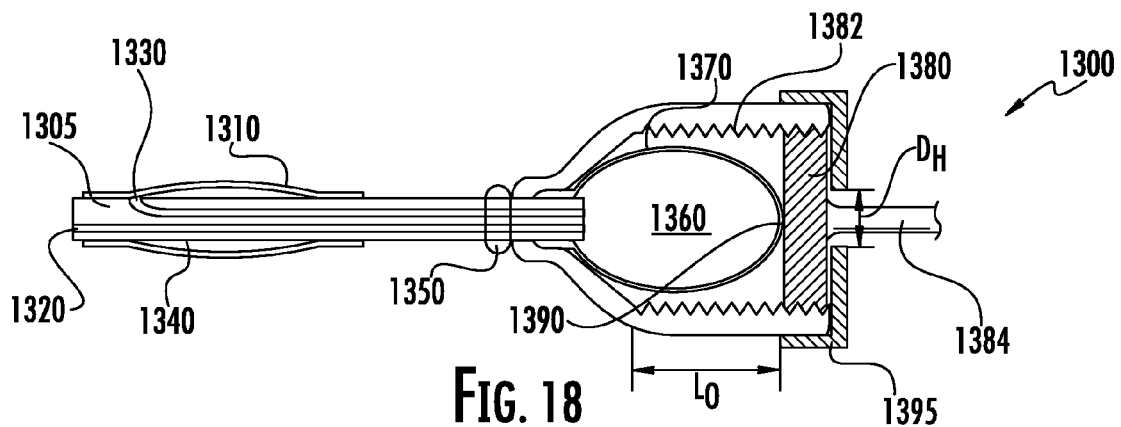
FIGS. 18-23 are schematic diagrams illustrating non-limiting examples of earplugs with modifiable attenuation.

FIGS. 18-23 illustrate non-limiting examples of earplugs with modifiable (tunable) attenuation. FIG. 18 illustrates an earpiece (e.g., earplug, headphone, hearing aid) that includes a first reservoir 1310 (e.g., Urethane balloon, silicon balloon) fed by a channel (tube) 1330 in a stent 1300. The stent 1300 can be fabricated from various materials (e.g., silicon, urethane, rubber) and can include internal channel (tubes), for example tubes 1330 and optional acoustic tube 1320. The stent can also be a multi-lumen (i.e., multi-passageway) stent where the channels/tubes are various lumens of the multi-lumen stent. The first reservoir 1310 can be connected to a second reservoir 1370 by way of the tube 1330. Thus a fluid 1360 can be transferred between the first reservoir 1310 and the second reservoir 1370 by pressing against the second reservoir 1370 or by pressing against the first reservoir 1310. Additionally the reservoirs (1370 and 1310) can be fabricated from stressed membranes (e.g., silicone) so that when fluid is inserted into the reservoirs a restoring force presses against the fluid 1360 by the membrane. For example if the second reservoir was fabricated from a compliant balloon with an initial state of collapse, then filling the second reservoir 1370 with fluid 1360 would stretch the membrane such that the membrane would seek to press against the fluid 1360. If the first reservoir restoring force caused by its membrane is less than that of the second reservoir 1370 then the fluid 1360 will move through tube 1330 into the first reservoir. Alternatively a structure can press against the second reservoir 1370 pushing against the fluid 1360 moving a portion of the fluid in to the first reservoir. FIG. 18 illustrates a non-limiting example of a structure that includes a piston head 1380, a front surface of the piston head 1390 connected to a stem 1384. The structure can lie within a housing that has optional internal threads 1382, which optional threads on piston head 1380 can engage so if one rotates the piston head one pushes the piston head front surface against the second reservoir 1370.

Note that in at least one exemplary embodiment the restoring force of the first reservoir 1310 can be such that the fluid remains in the second reservoir 1370 unless the volume of the second reservoir 1370 is decreased. Such a configuration can be used for an earplug where the portion to be inserted is collapsed into a minimal profile shape and upon insertion a user can move the structure so that the volume of the second reservoir 1370 decreases increasing the fluid in to the first reservoir, such that the first reservoir 1310 expands occluding a channel (e.g., ear canal) into which the earpiece is at least partially placed. Note that other channels can be used to convey acoustical energy across the first reservoir, for example the tube 1320 can be used to measure or emit sound to the left of the first reservoir as illustrated in FIG. 18.

Figure 19:
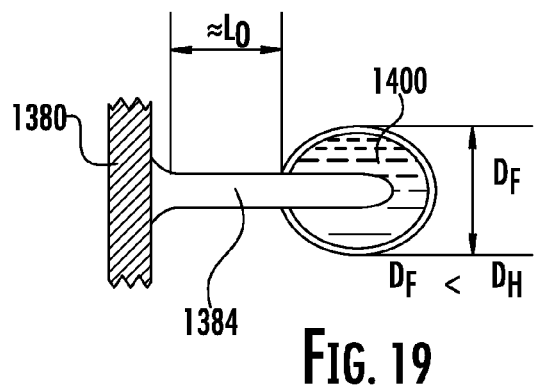

FIG. 19 illustrates a non-limiting example of a moveable structure discussed with reference to FIG. 18, where the stem 1384 is attached to a tab 1400 that a user can move (e.g., push, rotate) to move the structure toward or away from the second reservoir 1370.

Figure 20:
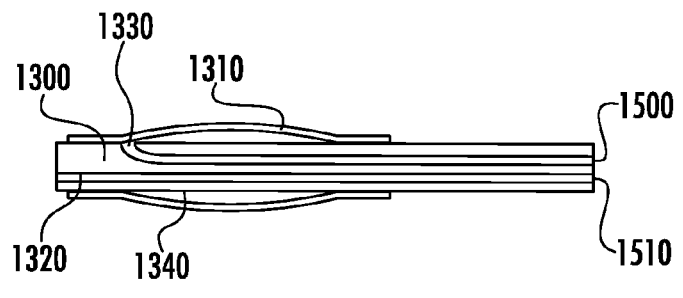
Figure 21:
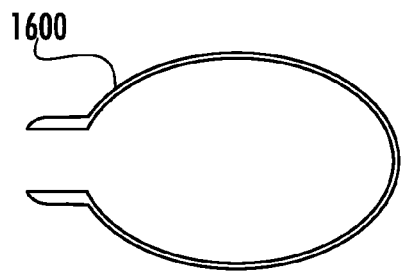
Figure 22:
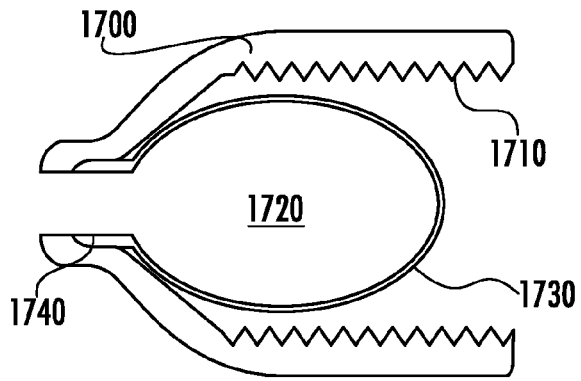
Figure 23:
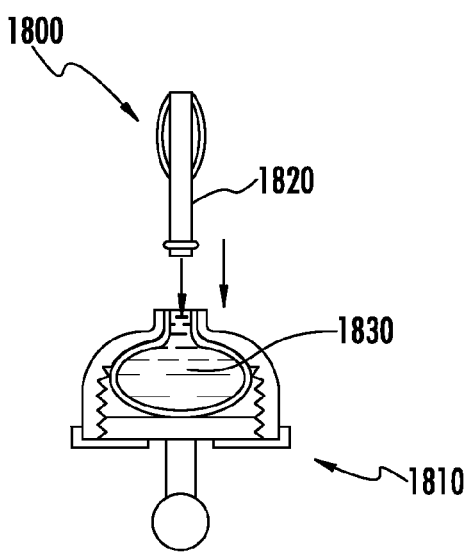
Figure 24:
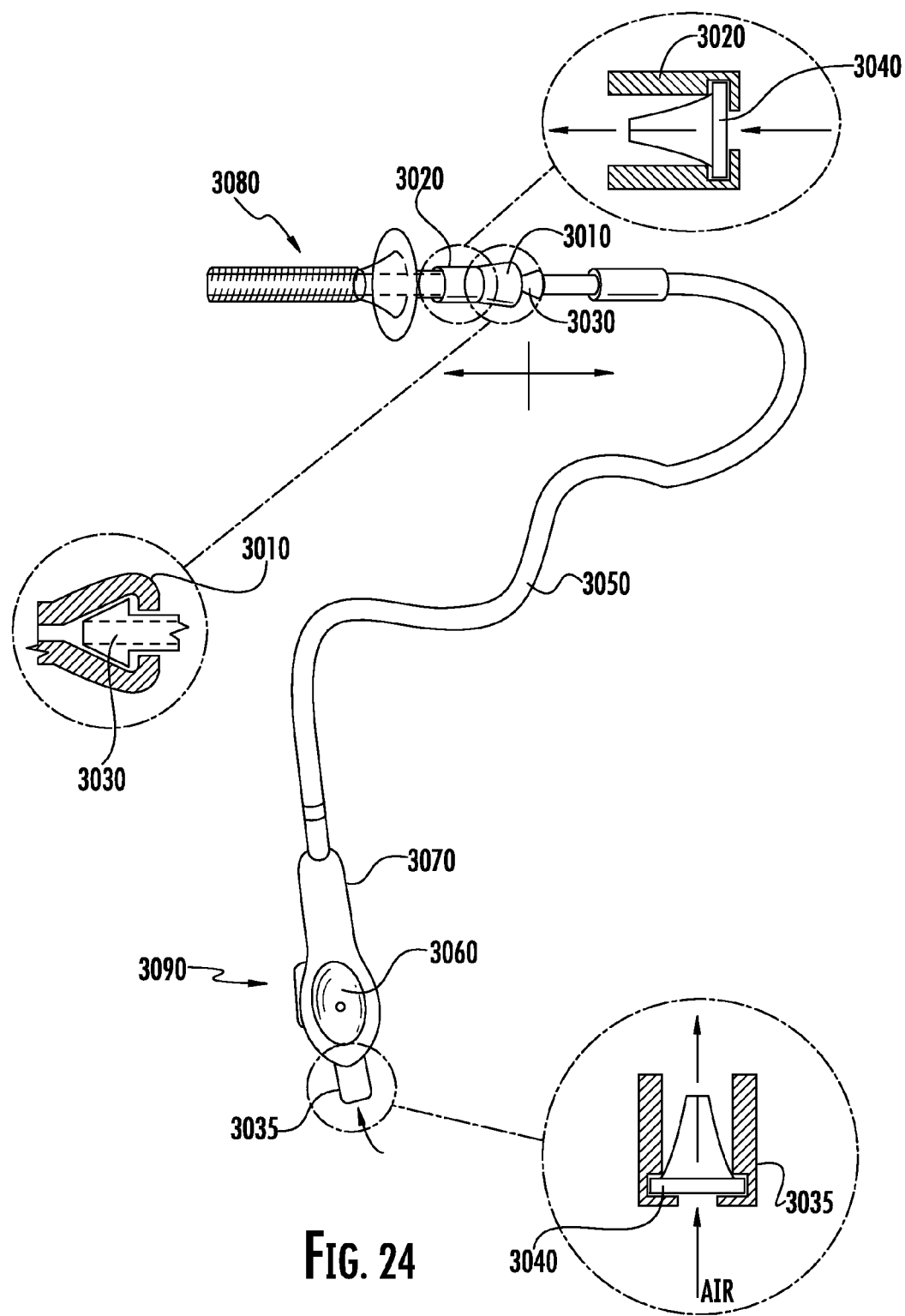
FIG. 24 is a schematic diagram illustrating a detachable earplug pumping system in accordance with at least one exemplary embodiment.

FIG. 20 illustrates an isolated view of the stent discussed with reference to FIG. 18. Note that for ease of manufacturing the stent can be similar to that used in an infant urology Foley catheter, which has an inflation tube 1330 and a flush tube 1320, where for an earplug the flush tube is sealed, for example by injecting a flexible curing material (e.g., Alumilite Flex 40™ casting rubber). A bladder 1600 (FIG. 21) having a preformed shape (e.g., non-compliant medical balloon) or flexible shape (e.g. compliant medical balloon) can be filled with the desired fluid then attached to the stent or to the housing and sealed (FIG. 22). The bladder 1730 can be attached 1740 to housing 1700 that can also include threads 1710. The fluid filled 1830 housing 1810 (FIG. 23) (e.g., fabricated from a plastic, hard rubber) can then be attached 1820 to the stent 1800, the structure screwed into threads in the housing, and a retainer cap 1395 attached to the housing (e.g., using loctite glue) restricting the movement of the structure. FIG. 24 illustrates a detachable earplug pumping system in accordance with at least one exemplary embodiment. The earpiece 3080 can be operatively attached by way of a tube 3050 to a finger pump 3090. The entire pump system (e.g., 3030, 3050, 3070, 3060, 3035) can be detachable from a pump insert port 3010. A pump seal valve 3040 in a sealing section 3020 in the earpiece 3080 generally allows one way flow and seals when the pump system is detached. The earpiece includes initially a deflated fluid reservoir which is fluid filled when the pump is actuated (e.g., finger pumped). The pump insert port 3010 allows general sealing with a detachable pumps insert interface 3030 (e.g., arrow head). The pump system can include a feed tube 3050 attached to the insert interface 3030. The feed tube can be attached to a pump body 3070 which includes a finger dimple 3060, for example fabricated from a restoring flexible material (e.g., rubber) that returns to its original shape after deformation. Thus deformation of the finger dimple 3060 forces fluid through feed tube 3050 and into the earpiece 3080. A one way valve (e.g., 3040) system 3035 feeds fluid (e.g., from the environment) into the pump body 3070 so by way of another deformation of the finger dimple 3060 fluid is available to be pumped into earpiece 3080.

Figure 25:
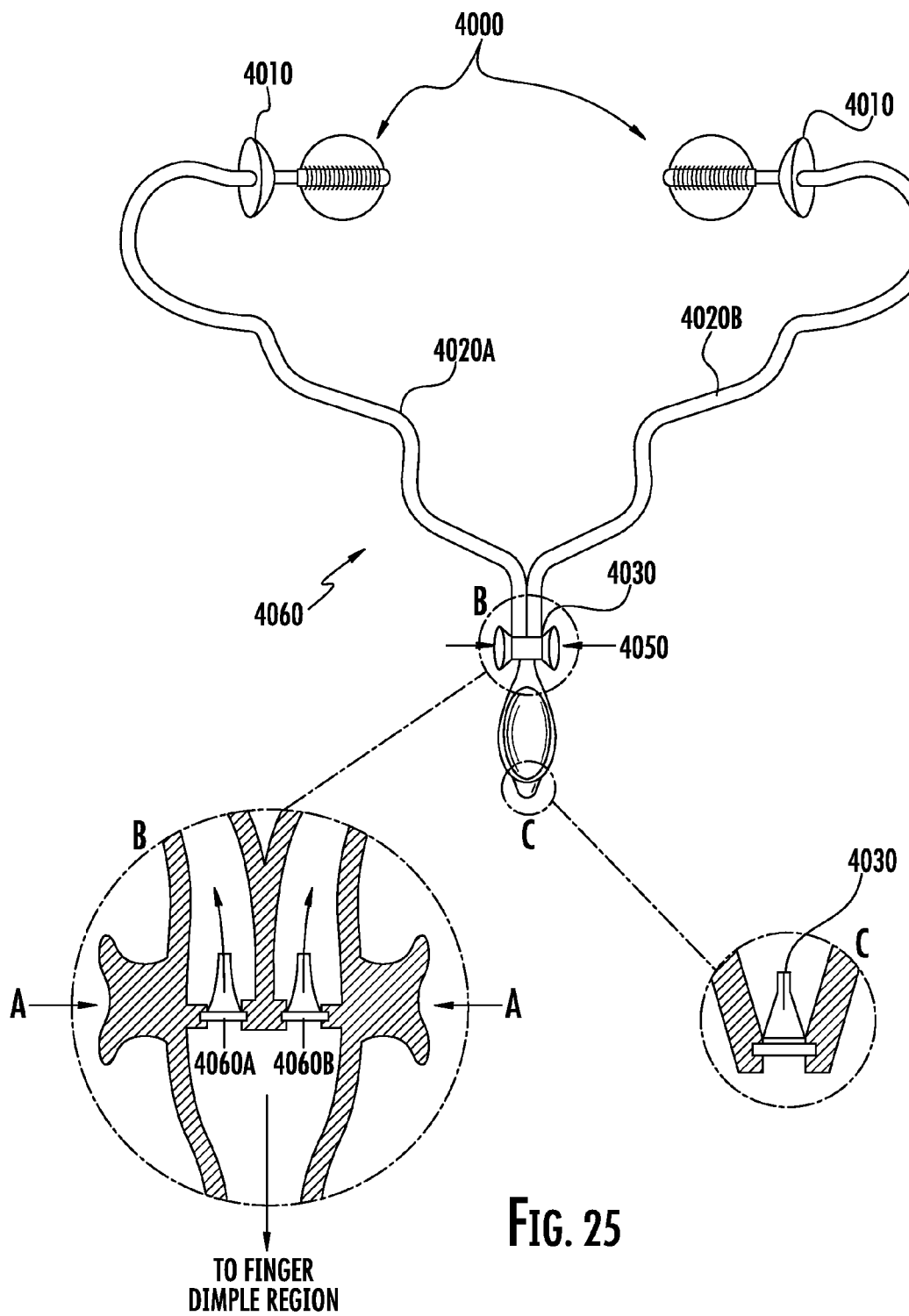
FIG. 25 is a schematic diagram illustrating a lanyard earplug system in accordance with at least one exemplary embodiment.

FIG. 25 illustrates a lanyard tube earplug system 4060 in accordance with at least one exemplary embodiment. Earpieces 4000 including optional stop flanges 4010 can be attached to a lanyard tube finger pump system 4060. The lanyard finger pump system can include two connected tubes 4020A and 4020B each feeding a separate earpiece 4000. The tubes 4020A and 4020B can be connected by way of one way valves 4030 to a squeeze release section 4050, which can be squeezed (A) to deflate the earpieces 4000. The pump section can include a finger dimple 4040 and an inlet one way valve C. The inlet one way valve C can include a one way valve 4030. The release section 4050 can include two one way valves, one 4060A associated with tube 4020A and the other 4060B associated with tube 4020B. As fluid is pushed through each one-way valve 4060A and 4060B the respective earpieces 4000 inflate. An optional one-way valve per tube (not shown) can be used to make sure that the maximum pressure in each tube 4020A and 4020B does not exceed a maximum value P max.

Figure 26:
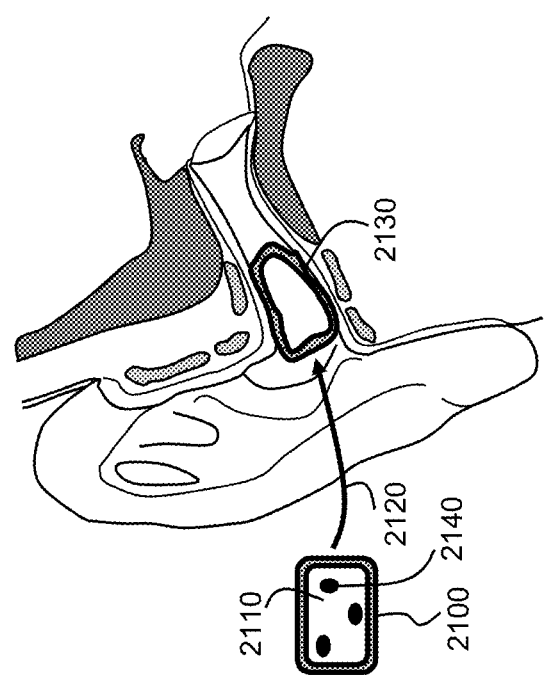
FIG. 26 is a schematic diagram illustrating a hearing protection device embodiment of the invention.

FIG. 26 illustrates at least one exemplary embodiment of an earplug (e.g., foam, polymer flange) with a hollow chamber 2100, which has a filler material (e.g., water, aphrons, water with solid particles suspended, oil with particles suspended 2140), that can be compressed and inserted 2120 into a compacted form 2130 in the ear canal. Note that while compacting the earplug the pressure of the interior can increase. The suspended particles or aphrons 2140 can be tailored with various materials tailored to the specific attenuation properties desired.

FIG. 27 illustrates an acoustic shaping panel 2700 in accordance with at least one exemplary embodiment and FIG. 28 illustrates a cross section of the panel illustrated in FIG. 27. The panel 2700 can include fastening elements 2871, or can have attachment elements on at least one side of the panel 2700 (e.g., Velcro™ attachment). Referring to FIG. 28, an incident 2841 acoustic wave 2840 (only one frequency illustrated for clarity) with amplitude 2842 passes through the panel 2700. Depending upon the desired acoustic shaping, the panel 2700 will modify different frequencies in various methods, for example reducing the amplitude (measured in Decibels or dB). The transmitted 2851 acoustic wave 2850 has a reduced amplitude 2852. The reduction amount of the incident amplitude (2852) is a function of the properties of the case (e.g. front 2810, back 2820, and rim 2830) of the panels and the properties of the medium 2880. The medium 2880 can be contained within a medium retainer container 2870 (e.g., a bladder). The medium 2880 can be inserted under various pressures to obtain various levels of amplitude reduction (e.g., attenuation).

FIG. 29 illustrates attachment of the panels of FIG. 27 on a wall 2900 in accordance with at least one exemplary embodiment. In the non-limiting example illustrated, the acoustic properties of a wall 2900 can be modified by adding multiple panels 2700 which are placed 2910 next to each other.

FIG. 30A illustrates cross section of an acoustic shaping panel in accordance with at least one exemplary embodiment. Referring to FIG. 30A, an incident 3041 acoustic wave 3040 (only one frequency illustrated for clarity) with amplitude 3042 passes through the panel. Depending upon the desired acoustic shaping, the panel will modify different frequencies in various methods, for example reducing the amplitude (measured in Decibels or dB). The transmitted 3051 acoustic wave 3050 has a reduced amplitude 3052. The medium 3080 can be contained within a medium retainer container 3070 (e.g., a bladder). FIG. 30B illustrates a closeup of the medium illustrated in FIG. 30A. In the non-limiting example illustrated in FIG. 30B the medium 3081 includes a suspension 3084, for example an aphron including a sheath 3083 and core 3082. For example the sheath 3083 could be an aqueous solution including a surfactant and a core 3082 including a mixture for example oil, or H2O+NaCl, or other mixtures.

FIGS. 31A, 31B, 31C, and 31D illustrate variations of cross sections of acoustic shaping panels in accordance with various exemplary embodiments. Panels can include various combinations of mediums to shape the acoustic properties of the panels, or a combination of individual panels. For example FIG. 31A illustrates two mediums 3110 and 3120 that can be combined to provide an overall panel property, while FIG. 31B illustrates two panels attached 3113 (e.g. via Velcro™, glue, screws, nails). Additional non-limiting examples are illustrated in FIG. 31C and FIG. 31D, where various combinations of mediums are combined to provide tailored acoustic shaping properties of the panels. For example FIG. 31C includes mediums 3141 and 3143 and fasteners 3171 and FIG. 31D includes multiple mediums 3191, 3192, and 3193.

FIGS. 32A, 32B, and 32C illustrate the configuration and operation of at least one exemplary embodiment of an earplug. The earplug 3200 includes a reservoir 3270, a moveable element 3260, a safety flange 3250, a valve 3240, a fluid channel 3230, a distal end reservoir 3220, and a distal end shaft 3210. The shaft 3210 can expand for example including regions of various thicknesses (e.g., a thin region 3245 and a thicker region 3247), or the shaft can have a port from the distal end reservoir to a flexible element around the distal end of the shaft 3210 which expands while the shaft remains generally constant.

FIG. 32C illustrates operation of the earplug Illustrated in FIG. 32A, where the moveable element 3260 is depressed (squeezed) for example by a user's fingers, to constrict the reservoir 3270. Any structure can be used to provide leverage for the user's fingers to depress the fluid reservoir. Here, opposing fingertip levers are used. Indeed, no structure is required and the user's fingers themselves can be used to depress the fluid reservoir, if desired. The constriction of reservoir 3270 forces the medium in the reservoir through the channel 3230 past the valve into the distal end reservoir 3220. The passing of the medium through the valve 3240 prevents the return of the medium into the reservoir 3270, thus once depressed the fluid remains in or near the distal end reservoir. If the shaft is flexible then the thin wall portion 3245 will expand 3280 in response B1 to the reservoir constriction A1. Note that a flexible element (not shown) can be encased around the shaft where fluid entering the distal reservoir travels via a port to the flexible element expanding the flexible element, which becomes the expandable element 3280. Note that a modification to the non-limiting example illustrated can include a second return valve that opens when a design pressure is reached, for example if one seeks to remove the earplug, when upon pulling the pressure is greater than a designed level (e.g., 400 mbar gauge pressure) then medium will flow from the distal reservoir 3220 to the reservoir 3270. FIG. 32C illustrates use of the earplug 3200 in an ear.

FIG. 33 illustrates another non-limiting example of an embodiment. The earplug 3300 is a foam plug with a reservoir and a finger tab 3310 to hold. A user squeezes C1 the foam to a smaller insertion form, which is inserted D1 into the ear canal 3320. Note that the reservoir can include a fluid foam medium, which can be compressed (for example where the gas bubbles get smaller upon compression), thus increasing the pressure of the inserted reservoir.

FIGS. 34A, 34B, and 34C illustrate the configuration and operation of at least one exemplary embodiment. The earplug 3400 includes a reservoir 3470, a moveable element 3460 with a distal end 3420, a safety flange 3450, a valve 3440, a fluid channel 3430, a distal end reservoir 3430 and at least one contact 3245. Note the safety flange 3450 can additionally include a flange reservoir. FIG. 34B illustrates the operation the earplug 3400, where the reservoir 3470 is constricted by moving E1 (squeezing) the moveable element 3460 forcing a portion of the medium through the valve 3440 into a distal end reservoir 3431 and optionally a safety flange reservoir. The medium moving into the distal reservoir 3431 allows the reservoir to remain constricted by the valve 3440 prohibiting backward flow. The contacts 3245 move as the moveable element 3460 is moved, where the contact 3245 press lightly against the walls of the ear canal securing the earplug. FIG. 34C illustrates use of the earplug 3400 in an ear.

FIGS. 35A, 35B, 35C, and 36 illustrate the configuration and operation of at least one exemplary embodiment. FIG. 35A illustrates a non-limiting example of an earplug embodiment 3500, including a deformable casing 3510 (e.g. foam), encircling a reservoir 3520, a valve 3540, a flexible distal end 3535, and optionally a flange 3530. FIG. 35B illustrates the operation of the earplug 3500, where depression G1 of the deformable casing 3510 constricts the reservoir 3520 forcing a portion of the medium past the valve into the flexible distal end 3535 (e.g., a balloon on a shaft, a flexible shaft with varying thickness) expanding H1 the flexible distal end 3535. The expansion of the flexible distal end 3535 can expand the flange 3531. In at least one embodiment a release mechanism can be included for a user to squeeze open a flexible valve, allowing passage of the medium from the flexible distal end 3535 back to the reservoir 3520. For example FIG. 35C illustrates an incorporated release mechanism that when pressed M1, effectively presses N1 on the flexible valve opening the valve for backflow. FIG. 36 illustrates use of the earplug 3500 in an ear.

Although considerable discussion has been included with respect to use in earplugs, additional embodiments of the invention can be used in other systems and devices that can benefit from controlling the acoustic spectrum passing through the device. For example, helmets, flexible wrap that is wrapped around devices for acoustic isolation, tool handles (e.g., jackhammers), around the hull of ships to mitigate acoustic loss, and other uses one of ordinary skill in the relevant art would know. For example FIG. 37 and FIG. 38 illustrates an embodiment used in a helmet 3700 (e.g. for use on aircraft carriers or other noisy environments) where several liners 3710 and 3720 (although a single liner can be used), where the liners (3710 and/or 3720) each can include different fluid mediums to shape the acoustic profiles entering the helmet 3700.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. Where a range of values is provided in this specification, each value between the upper and lower limits of that range is also specifically disclosed. The upper and lower limits of these smaller ranges may independently be included or excluded in the range as well. Additionally, although specific numbers may be quoted in the claims, it is intended that a number close to the one stated is also within the intended scope, such that the stated number is construed to mean "about." As used in this specification, the singular forms "a," "an," and "the" include plural referents unless the context clearly dictates otherwise. Additionally, if words are used to described how one component is disposed relative to another such as "circumferential," "radial," "linearly," "orthogonal," and "perpendicular," the intended meaning is "substantially" "circumferential," "radial," linearly," "orthogonal," and "perpendicular." Likewise, terms of degree, such as "uniform," "non-uniform," or "flat," are intended to encompass embodiments that may be substantially so. Further, it is intended that the specification and examples be considered as exemplary in nature and that variations that do not depart from the essence of the invention are intended to be within the scope of the invention. The references cited in this disclosure provide general background about the technology or components that can be incorporated into devices, systems and methods of the invention, each being relied on for purposes of providing a detailed disclosure of the invention and each incorporated by reference herein in its entirety.

The invention claimed is:

1. An earplug comprising:
a reservoir, where the reservoir includes a flowable medium;
a valve;
a channel; and
a flexible distal end,
where the reservoir is operationally connected to the distal end by the channel, where the valve is in the channel between the reservoir and the distal end,
where the valve is configured to allow the flowable medium to flow from the reservoir to the distal end,
where the flowable medium is selected to attenuate at least one acoustic frequency within a first acoustic frequency bandwidth, and
where an operational pressure of the flowable medium and any second flowable medium surrounded by the flexible distal end is selected to be within a gauge pressure range during use.

2. The earplug according to claim 1, further comprising:
a safety limiter flange, where the safety limiter flange diameter is designed to limit earplug insertion into the ear canal beyond a designed distance.

3. The earplug according to claim 2, further comprising:
a distal end flange, where the distal end flange is expandable when the flexible distal end is expanded.

4. The earplug according to claim 1, where the first acoustic frequency bandwidth is between 250 Hz to 4000 Hz, where the pressure range is between 100 mbar and 1000 mbar gauge pressure.

5. The earplug according to claim 4, where the transmitted acoustic spectrum is flat across the first acoustic frequency bandwidth within about +/−5 dB.

6. The earplug according to claim 4, where the medium is at least one of air, liquid, foam, water, oil, water with a salt, water with alcohol, alcohol, water with oil, aphrons, oil with suspended particles, water with suspended solid particles, water with suspended gelatinous particles, water and sugar, liquid with gas bubbles, and carbonated water.

7. The earplug according to claim 6, further comprising:
a first movable element; and
a second movable element, where the first and second moveable elements are configured to be moved by a user's fingers, where movement of the first and second moveable elements compress the reservoir, where upon compression the medium flows through the valve into the distal end where the valve restricts flow back to the reservoir.

8. The earplug according to claim 6, further comprising:
a release mechanism, where the release mechanism is configured to be operated by a user to allow medium to flow from the distal end to the reservoir.

9. An earplug comprising:
a reservoir; and
a medium, where the medium is contained within the reservoir, where the reservoir is deformable and configured to expand back to a precompressed state when compressed and released, where the reservoir is configured to be compressed by a user's fingers and inserted into an ear canal, where upon or after insertion into the ear canal the reservoir is configured to expand, applying pressure to the ear canal wall.

10. The earplug according to claim 9, further comprising:
a finger tab or stem, where the finger tab or stem is configured to allow gripping of the tab with at least two fingers, where a user can pull on the tab to extract the earplug from the ear canal.

11. The earplug according to claim 10, where the medium is at least one of air, liquid, foam, water, oil, water with a salt, water with alcohol, alcohol, water with oil, aphrons, oil with suspended particles, water with suspended solid particles, water with suspended gelatinous particles, water and sugar, liquid with gas bubbles, and carbonated water.

12. An acoustic shaping panel comprising:
a front;
a back;
a rim; and
a medium container, where the medium container is configured to be pressurized, where the medium container contains a medium, where the front, back, and rim substantially encloses the container, where the medium is selected to shape an incident acoustic spectrum to a designed transmitted acoustic spectrum.

13. The acoustic shaping panel according to claim 12, where the transmitted acoustic spectrum is flat across the spectrum within about +/−5 dB from 250 Hz to 4000 Hz.

14. The acoustic shaping panel according to claim 12, where the medium is at an operational pressure during use that is within a pressure range.

15. The acoustic shaping panel according to claim 14, where the pressure range is from 200 mbar to 2000 mbar gauge pressure.

16. The acoustic shaping panel according to claim 15, where the medium is at least one of air, liquid, foam, water, oil, water with a salt, water with alcohol, alcohol, water with oil, aphrons, oil with suspended particles, water with suspended solid particles, water with suspended gelatinous particles, water and sugar, liquid with gas bubbles, and carbonated water.

17. The acoustic panel according to claim 16, where the panel is configured to be a liner which, where the liner is configured to be inserted into the inside of a helmet.

18. The acoustic panel according to claim 17, where the fluid medium reduces the amplitude of transmitted acoustic spectrum above 500 Hz by at least 15 dB from the incident acoustic spectrum.

19. The acoustic panel according to claim 18, where the transmitted acoustic spectrum is flat across the spectrum within about +/−5 dB from 250 Hz to 4000 Hz.

\* \* \* \* \*